(12) United States Patent
Galley et al.

(10) Patent No.: US 10,458,973 B2
(45) Date of Patent: Oct. 29, 2019

(54) HANDHELD DIABETES MANAGEMENT DEVICE WITH BOLUS CALCULATOR

(75) Inventors: Paul J. Galley, Cumberland, IN (US); Alan M. Greenburg, Indianapolis, IN (US); Marshall M. Parker, Indianapolis, IN (US); John F. Price, McCordsville, IN (US); Robin S. Wagner, Indianapolis, IN (US); Richard W. Wilson, Fortville, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 1327 days.

(21) Appl. No.: 13/593,557

(22) Filed: Aug. 24, 2012

(65) Prior Publication Data

US 2014/0058237 A1    Feb. 27, 2014

Related U.S. Application Data

(63) Continuation-in-part of application No. 12/976,507, filed on Dec. 22, 2010, now Pat. No. 8,615,366.

(51) Int. Cl.
*G01N 33/48* (2006.01)
*G01N 33/487* (2006.01)
(Continued)

(52) U.S. Cl.
CPC ... *G01N 33/48792* (2013.01); *A61B 5/14532* (2013.01); *A61B 5/157* (2013.01); *A61B 5/150022* (2013.01)

(58) Field of Classification Search
None
See application file for complete search history.

(56) References Cited

U.S. PATENT DOCUMENTS 5,840,020 A    11/1998 Heinonen et al.
5,971,922 A    10/1999 Arita et al.
(Continued)

FOREIGN PATENT DOCUMENTS

WO    WO-2004084820 A2    10/2004
WO    WO-2009048462 A1    4/2009
WO    WO-2011153519 A2    12/2011

OTHER PUBLICATIONS

Smiths Medical MD, Inc., Deltec Cozmo®, Fine Tuning Your Deltec Cozmo® Insulin Pump Settings, Overnight Basal Rate Test Instructions, 2 pp. Date Unknown.
(Continued)

*Primary Examiner* — Larry D Riggs, II
(74) *Attorney, Agent, or Firm* — Harness, Dickey & Pierce, P.L.C.

(57) ABSTRACT

According to some embodiments of the present disclosure, a device and method for determining an allowable amount of blood glucose (bG) of a patient is disclosed. The method further includes receiving a current bG measurement, determining a target bG value, and determining a correction delta bG value based on one or more advice history records. The method includes determining a correction meal rise value and determining a maximum allowed bG value based on the target bG value, the correction delta bG value, and the correction meal rise value. The method includes setting the allowable amount of bG value equal to the maximum allowed bG value when the current bG measurement is greater than the target bG value and determining the allowable amount of bG value using the target bG value and the correction delta bG value when the current bG measurement is less than the target bG value.

19 Claims, 18 Drawing Sheets

(51) Int. Cl.
*A61B 5/145* (2006.01)
*A61B 5/157* (2006.01)
*A61B 5/15* (2006.01)

(56) References Cited

U.S. PATENT DOCUMENTS

| | | |
|---|---|---|
| 7,291,107 B2 | 11/2007 | Hellwig et al. |
| 7,404,796 B2 | 7/2008 | Ginsberg |
| 7,445,609 B2 | 11/2008 | Bunke et al. |
| 7,553,281 B2 | 6/2009 | Hellwig et al. |
| 7,869,851 B2 | 1/2011 | Hellwig et al. |
| 7,927,313 B2 | 4/2011 | Stewart et al. |
| 8,118,770 B2 | 2/2012 | Galley et al. |
| 8,226,891 B2 | 7/2012 | Sloan et al. |
| 2003/0055570 A1 | 3/2003 | Ribeiro |
| 2004/0172284 A1 | 9/2004 | Sullivan et al. |
| 2005/0192494 A1 | 9/2005 | Ginsberg |
| 2006/0047192 A1 | 3/2006 | Hellwig et al. |
| 2006/0137695 A1 | 6/2006 | Hellwig et al. |
| 2008/0058628 A1 | 3/2008 | Hellwig et al. |
| 2008/0139910 A1 | 6/2008 | Mastrototaro et al. |
| 2008/0172026 A1 | 7/2008 | Blomquist |
| 2008/0172028 A1 | 7/2008 | Blomquist |
| 2008/0183060 A1 | 7/2008 | Steil et al. |
| 2009/0030733 A1 | 1/2009 | Cohen et al. |
| 2009/0036753 A1 | 2/2009 | King |
| 2009/0105570 A1 | 4/2009 | Sloan et al. |
| 2010/0017141 A1 | 1/2010 | Campbell et al. |
| 2010/0057043 A1 | 3/2010 | Kovatchev et al. |
| 2010/0160740 A1 | 6/2010 | Cohen et al. |
| 2010/0160757 A1 | 6/2010 | Weinert et al. |
| 2010/0160759 A1 | 6/2010 | Celentano et al. |
| 2010/0161346 A1 | 6/2010 | Getschmann et al. |
| 2010/0168660 A1 | 7/2010 | Galley et al. |
| 2010/0174553 A1 | 7/2010 | Kaufman et al. |
| 2010/0204557 A1 | 8/2010 | Kiaie et al. |
| 2010/0212675 A1 | 8/2010 | Walling et al. |
| 2010/0218132 A1 | 8/2010 | Soni et al. |
| 2010/0249530 A1 | 9/2010 | Rankers et al. |
| 2010/0331650 A1 | 12/2010 | Batman et al. |
| 2011/0054439 A1 | 3/2011 | Yodfat et al. |
| 2011/0098548 A1 | 4/2011 | Budiman et al. |
| 2011/0237917 A1 | 9/2011 | Roy et al. |

OTHER PUBLICATIONS

Smiths Medical MD, Inc., Deltec Cozmo®, User Manual, Deltec Cozmo® Insulin Pump, 245 pp, Date Unknown.
Pardigm 512/517 Infusion Pumps, pp. 1-162, XP055110670, (Jan. 2005).

HANDHELD DIABETES MANAGEMENT DEVICE WITH BOLUS CALCULATOR

CROSS-REFERENCE TO RELATED APPLICATION

This application is a continuation-in-part of U.S. Ser. No. 12/976,507 filed Dec. 22, 2010. The disclosure of the above application is incorporated herein by reference.

FIELD

This disclosure relates to diabetes care medical devices used for diagnostics and therapy, and more particularly to a diabetes management device incorporating a bolus calculator that determines a maximum allowed blood glucose level of a patient to compare to a current blood glucose measurement.

BACKGROUND

The statements in this section merely provide background information related to the present disclosure and may not constitute prior art.

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. Its incidence is increasing rapidly, and it is estimated that between 2005 and 2030, the number of deaths from diabetes will double. In the United States, nearly 24 million Americans have diabetes with an estimated 25 percent of seniors age 60 and older being affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Management of diabetes is complex as the level of blood glucose entering the bloodstream is dynamic. The variation of insulin that controls the transport of glucose out of the bloodstream also complicates diabetes management. Blood glucose levels are sensitive to diet and exercise, but also can be affected by sleep, stress, smoking, travel, illness, menses, and other psychological and lifestyle factors unique to individual patients. The dynamic nature of blood glucose and insulin, and all other factors affecting blood glucose, often require a person with diabetes to understand ongoing patterns and forecast blood glucose levels (or at least understand the actions that raise or lower glucose in the body). Therefore, therapy in the form of insulin or oral medications, or both, can be timed to maintain blood glucose levels in an appropriate range.

Management of diabetes is often highly intrusive because of the need to consistently obtain reliable diagnostic information, follow prescribed therapy, and manage lifestyle on a daily basis. Daily diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an insulin pen, an ambulatory infusion pump, or a combination of such devices. With insulin therapy, calculating the amount of insulin to be injected can require determining meal composition of carbohydrates, fat and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data that are acquired from medical devices, personal healthcare devices, patient recorded information, healthcare professional biomarker data, prescribed medications and recorded information. Medical devices including self-monitoring bG meters, continuous glucose monitors, ambulatory insulin infusion pumps, diabetes analysis software, and diabetes device configuration software each of which generates and/or manages large amounts of diagnostic and prescriptive data. Personal healthcare devices include weight scales, pedometers and blood pressure cuffs. Patient recorded information includes information relating to meals, exercise and lifestyle as well as prescription and non-prescription medications. Healthcare professional biomarker data includes HbA1C, fasting glucose, cholesterol, triglycerides and glucose tolerance test results. Healthcare professional recorded information includes therapy and other information relating to the patient's treatment.

There is a need for a patient device to aggregate, manipulate, manage, present, and communicate diagnostic data and prescriptive data from medical devices, personal healthcare devices, patient recorded information, biomarker information and recorded information in an efficient manner to improve the care and health of a person with diabetes, so the person with diabetes can lead a full life and reduce the risk of complications from diabetes.

Additionally, there is a need for a diabetes management device that is able to provide an even more accurate bolus recommendation to the user based on various user inputs that take into account recent activities and events which may have an effect on the bG level of a patient to thus enhance the accuracy, convenience and/or efficiency of the device in generating a recommended bolus or a suggested carbohydrate amount for the user.

SUMMARY

According to some embodiments of the present disclosure, a computer-implemented method for determining an allowable amount of blood glucose (bG) of a patient is disclosed. The allowable amount of blood glucose is used to calculate a bolus recommendation for a patient. The method includes maintaining, at one or more processors, a plurality of active advice history records, each of the plurality of active advice history records having been generated during a predetermined time period relative to a current time, and each of the plurality of active advice history records identifying data relating to one or more bG influencing events and including a time corresponding to the one or more bG influencing events. The method further includes receiving a current bG measurement corresponding to the patient, the current bG measurement indicating a current bG level of the patient. The method also includes determining a target bG value for the patient, the target bG value corresponding to a desired bG level for the patient. The method also includes determining a correction delta bG value based on one or more records of the plurality of active advice history records, the correction delta bG value being indicative of an aggregated bG lowering effect of the events defined in the one or more active advice history records on a bG value of the patient. The method also includes determining a correction meal rise value based on a specific active advice history record of the plurality of active advice history records, the correction meal rise value being indicative of an amount the bG level of the patient can increase with respect to the target bG value without requiring a correction bolus. The method further includes determining a maximum allowed bG value based on the target bG value, the correction delta bG value, and the correction meal rise value. The method further includes comparing the current bG measurement to the target bG value and setting the allowable amount of bG value equal to the maximum allowed bG value when the current bG measurement is greater than the target bG value. The method also includes setting the allowable amount of bG value using the target bG value and the correction delta bG value and excluding the correction meal rise value when the current bG measurement is less than the target bG value. The method further includes storing the allowable amount of bG value.

According to some embodiments of the present disclosure, when the current bG measurement is less than the target bG value, the allowable amount of bG value is set equal to the sum of the target bG value and the correction delta bG value.

In some embodiments determining the correction delta bG value further includes, for each active advice history record of the plurality of active advice history records: analyzing the active advice history record to determine a bG lowering effect associated with the active advice history record and aggregating the bG lowering effect associated with previous bG lowering effects corresponding to previously analyzed active advice history records. The correction delta bG value is determined based on the aggregation of the bG lowering effect of all of the plurality of active advice history records.

In some embodiments determining the correction delta bG value further includes, for each active advice history record of the plurality of active advice history records: after aggregating the bG lowering effect associated with the previous bG lowering effects corresponding to the previously analyzed active history records, determining whether the aggregated bG lowering effect is less than zero, and when the aggregated bG lowering effect is less than zero, setting the aggregated bG lowering effect equal to zero. The correction delta bG value is determined based on the aggregation of the bG lowering effect of all of the plurality of active advice history records and the active advice history records are analyzed sequentially beginning with an oldest active advice history record.

In some embodiments analyzing the active advice history record further includes determining whether a bG measurement defined in the active advice history record is below a bG threshold. When the bG measurement defined in the active history record is less than the bG threshold, the bG lowering effect associated with the active advice history record is determined based on a carbohydrate amount defined in the active advice history record. When the bG measurement defined in the active history record is greater than the bG threshold, the bG lowering effect associated with the active advice history record is determined based on an insulin amount defined in the active advice history record.

According to some embodiments of the present disclosure, analyzing the active advice history record further includes determining an amount of time that that has lapsed since the active advice history record has been generated and comparing the amount of time to an offset time associated with the active advice history record, the offset time indicating a first duration during which the events defined in the active advice history record have a full effect on the bG level of the patient. When the amount of time is greater than the offset time, the bG lowering effect associated with the active advice history record is determined based on:

$$\frac{WorkingDeltabG}{Acting\_Time - Offset\_Time} \times (Acting\_Time - Time)$$

where WorkingDeltabG is the bG lowering effect associated with the active advice history record, Acting_Time is a second duration during which the events defined in the active advice history records effect the bG level of a patient, Offset_Time is the offset time, and Time is the amount of time.

According to some embodiments of the present disclosure, determining the correction meal rise value includes ensuring the events defined in the specific active advice history record include a bolus being associated with a carbohydrate intake event where the carbohydrate intake is greater than a predetermined threshold and further include an indication that insulin was administered to the patient and correspond to a time that is temporally closer to a current time than other active advice history records in the plurality of active advice history records defining events that include a meal bolus and a confirmation of insulin.

According to some embodiments of the present disclosure, determining the correction meal rise value further includes determining an amount of time that has lapsed since the time corresponding to the specific active advice history record and comparing the amount of time to an offset time associated with the specific active advice history record. When the amount of time is less than the offset time, the correction meal rise value is set equal to a full meal rise value defined in the specific active advice history record. When the amount of time is greater than the offset time, the correction meal rise value is set equal to an adjusted meal rise value based on the amount of time and the full meal rise value.

In some embodiments of the present disclosure the adjusted meal rise value is determined according to:

$$\frac{Meal\_Rise}{Acting\_Time - Offset\_Time} \times (Acting\_Time - Time)$$

where Meal_Rise is the full meal rise value associated with the specific active advice history record, Offset_Time is a first duration during which the events defined in the specific active advice history record have a full effect on the bG level of the patient, Acting_Time is a second duration during which the events defined in the specific active advice history records effect the bG level of a patient, and Time is the amount of time.

According to some embodiments of the present disclosure, a method for determining a correction meal rise value is disclosed. The correction meal rise value is indicative of an amount the bG level of the patient can increase with respect to a target bG value without requiring a correction bolus. The method includes maintaining a plurality of active advice history records, each of the plurality of active advice history records having been generated during a predetermined time period relative to a current time, and each of the plurality of active advice history records identifying data relating to a bG influencing event and including a time corresponding to the bG influencing event. The method further includes identifying, at one or more processors, a specific active advice history record of the plurality of active advice history records, wherein the events defined in the specific active advice history record include a bolus being associated with a carbohydrate intake event where the carbohydrate intake is greater than a predetermined threshold and further including an indication that insulin was administered to the patient in response to the bolus and correspond to a time that is more recent to a current time than other active advice history records in the plurality of active advice history records defining events that include a meal bolus and a confirmation of insulin. The method also includes determining an amount of time that has lapsed since the time corresponding to the specific active advice history record, comparing the amount of time to a predetermined time threshold, and setting the correction meal rise value equal to a full meal rise value as defined in the specific active advice history record when the amount of time is less than the predetermined time threshold. The method also includes setting the correction meal rise value equal to an adjusted meal rise value based on the amount of time and the full meal rise value when the amount of time is greater than the predetermined time threshold.

In some embodiments of the present disclosure, the adjusted meal rise value is determined according to a predetermined linear function.

In some embodiments of the present disclosure, the adjusted meal rise value is determined according to:

$$\frac{Meal\_Rise}{Acting\_Time - Offset\_Time} \times (Acting\_Time - Time)$$

where Meal_Rise is the full meal rise value associated with the specific active advice history record, Offset_Time is a first duration during which the events defined in the specific active advice history record have a full effect on the bG level of the patient, Acting_Time is a second duration during which the events defined in the specific active advice history records effect the bG level of a patient, and Time is the amount of time.

According to some embodiments of the present disclosure a diabetes management device configured to determine an allowable amount of blood glucose (bG) of a patient is disclosed. The allowable amount of blood glucose is used to calculate a bolus recommendation for a patient. The device includes an advice history records database that stores a plurality of active advice history records, each of the plurality of active advice history records having been generated during a predetermined time period relative to a current time, and each of the plurality of active advice history records identifying data relating to one or more bG influencing events and including a time corresponding to the one or more bG influencing events. The device further includes a computer-readable medium storing computer-readable instructions and one or more processors configured to execute the computer-readable instructions. The computer-readable instructions, when executed by the one or more processors, cause the one or more processors to receive a current bG measurement corresponding to the patient, the current bG measurement indicating a current bG level of the patient. The computer readable instructions further cause the one or more processors to determine a target bG value for the patient, the target bG value corresponding to a desired bG level for the patient. The computer readable instructions further cause the one or more processors to determine a correction delta bG value based on one or more records of the plurality of active advice history records, the correction delta bG value being indicative of an aggregated bG lowering effect of the events defined in the one or more active advice history records on a bG value of the patient. The computer readable instructions also cause the one or more processors to determine a correction meal rise value based on a specific active advice history record of the plurality of active advice history records, the correction meal rise value being indicative of an amount the bG level of the patient can increase with respect to the target bG value without requiring a correction bolus. The computer readable instructions further cause the one or more processors to determine, a maximum allowed bG value based on the target bG value, the correction delta bG value, and the correction meal rise value and to compare the current bG measurement to the target bG value. The computer readable instructions further cause the one or more processors to set the allowable amount of bG value equal to the maximum allowed bG value when the current bG measurement is greater than the target bG value. The computer readable instructions further cause the one or more processors to determine the allowable amount of bG value using the target bG value and the correction delta bG value and excluding the correction meal rise value when the current bG measurement is less than the target bG value. The computer readable instructions further cause the one or more processors to store the allowable amount of bG value.

In some embodiments of the present disclosure, the computer readable instructions, when executed by the one or more processors, cause the one or more processors to set the allowable amount of bG value equal to the sum of the target bG value and the correction delta bG value when the current bG measurement is less than the target bG value.

In some embodiments of the present disclosure, the computer readable instructions, when executed by the one or more processors, further cause the one or more processors to, for each active advice history record of the plurality of active advice history records, analyze the active advice history record to determine a bG lowering effect associated with the active advice history record and aggregate the bG lowering effect associated with previous bG lowering effects corresponding to previously analyzed active advice history records. The correction delta bG value is determined based on the aggregation of the bG lowering effect of all of the plurality of active advice history records and the active advice history records are analyzed sequentially beginning with an oldest active advice history record.

In some embodiments of the present disclosure, the computer readable instructions, when executed by the one or more processors, further cause the one or more processors to, for each active advice history record of the plurality of active advice history records: determine whether the aggregated bG lowering effect is less than zero after aggregating the bG lowering effect associated with the previous bG lowering effects corresponding to the previously analyzed active history records, and to set the aggregated bG lowering effect equal to zero when the aggregated bG lowering effect is less than zero.

In some embodiments of the present disclosure the computer readable instructions, when executed by the one or more processors, further cause the one or more processors to determine whether a bG measurement defined in the active advice history record is below a bG threshold, determine the bG lowering effect associated with the active advice history record based on a carbohydrate amount defined in the active advice history record when the bG measurement defined in the active history record is less than the bG threshold, and determine the bG lowering effect associated with the active advice history record based on an insulin amount defined in the active advice history record when the bG measurement defined in the active history record is greater than the bG threshold.

In some embodiments of the present disclosure the computer readable instructions, when executed by the one or more processors, further cause the one or more processors to determine an amount of time that that has lapsed since the active advice history record has been generated and compare the amount of time to an offset time associated with the active advice history record, the offset time indicating a first duration during which the events in the active advice history record have a full effect on the bG level of the patient. When the amount of time is greater than the offset time, adjust the bG lowering effect associated with the active advice history record based on:

$$\frac{WorkingDeltabG}{Acting\_Time - Offset\_Time} \times (Acting\_Time - Time)$$

where WorkingDeltabG is the bG lowering effect associated with the active advice history record, Acting_Time is a second duration during which the events defined in the active advice history records effect the bG level of a patient, Offset_Time is the offset time, and Time is the amount of time.

According to some embodiments of the present disclosure, determining the correction meal rise value further includes ensuring events defined in the specific active advice history record include a bolus being associated with a carbohydrate intake event where the carbohydrate intake is greater than a predetermined threshold and further include an indication that insulin was administered to the patient and correspond to a time that is more recent to a current time than other active advice history records in the plurality of active advice history records defining events that include a meal bolus and a confirmation of insulin.

In some embodiments of the present disclosure the computer readable instructions, when executed by the one or more processors, further cause the one or more processors to determine an amount of time that has lapsed since the time corresponding to the specific active advice history record, compare the amount of time to an offset time associated with the specific active advice history record, and set the correction meal rise value equal to a full meal rise value defined in the specific active advice history record when the amount of time is less than the offset time. When the amount of time is greater than the offset time, set the correction meal rise value equal to:

$$\frac{Meal\_Rise}{Acting\_Time - Offset\_Time} \times (Acting\_Time - Time)$$

where Meal_Rise is the full meal rise value associated with the specific active advice history record, Offset_Time is a first duration during which the events defined in the specific active advice history record have a full effect on the bG level of the patient, Acting_Time is a second duration during which the events defined in the specific active advice history records effect the bG level of a patient, and Time is the amount of time.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The following figures are selected embodiments of the diabetes manager with enhanced data capability and related system embodiments and information.

DETAILED DESCRIPTION

The following description is merely exemplary in nature and is not intended to limit the present disclosure, application, or uses.

Figure 1:
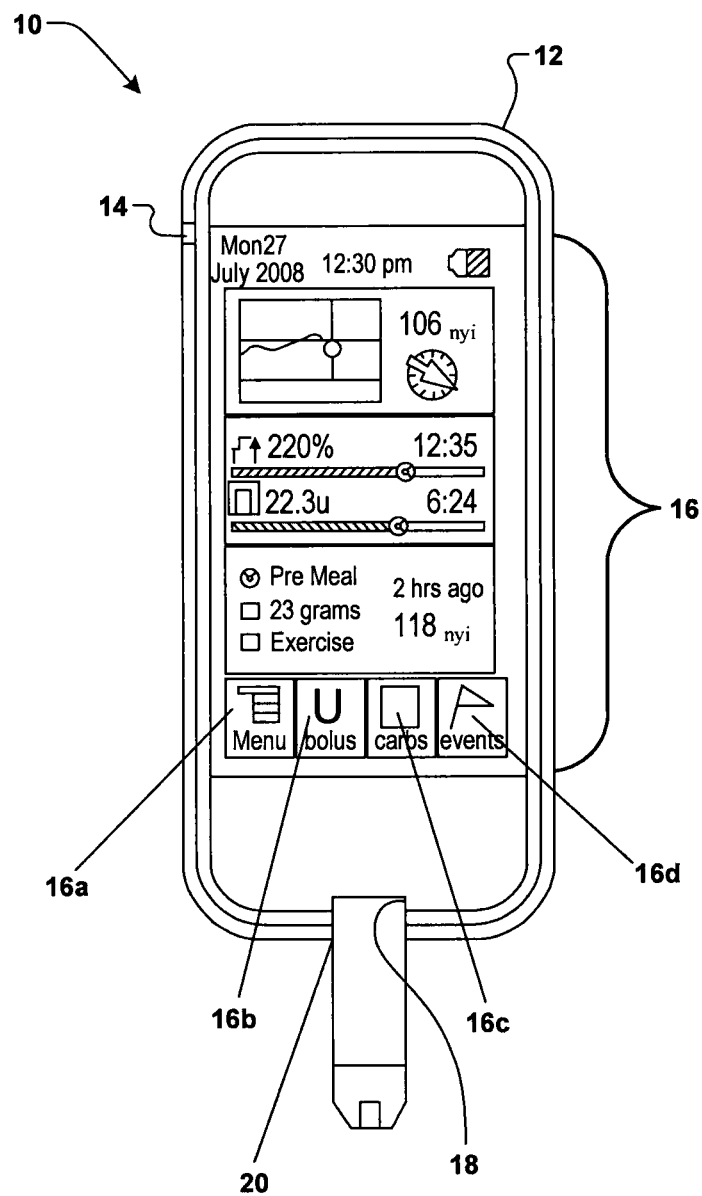
FIG. 1 is a perspective view of one embodiment of a handheld diabetes bG management device in accordance with the present disclosure.

Referring to FIG. 1, there is shown a high level drawing of one embodiment of a handheld, diabetes management device 10 that may be used in measuring the blood glucose (bG) of a patient and implementing a bolus calculation or carbohydrate suggestion. Typically the device 10 includes a housing 12 that may contain user unit control switches 14 (e.g., ON/OFF), a touchscreen display 16, and a port 18 into which a bG test strip 20 may be inserted. The display 16 may display user selectable options for allowing the user to access a software driven menu 16a of various selections, a selection 16b for allowing the user to enter bolus information, a selection 16c for enabling the user to enter carbohydrate information for snacks or meals, and a selection 16d for allowing the user to enter information pertaining to health events (e.g., meals, exercise, periods of stress, periodic physiological events such as a menstrual cycle, etc.) that may affect the user's bG measurement being read by the device 10. Although the display 16 will be described herein as a touchscreen display, it will be appreciated that any other suitable form of display may be incorporated (e.g., LED, etc.). If a touchscreen display is not used, the user control switches 14 may need to include specific buttons or controls by which the user is able to select various options and input markers needed to carry out the bolus calculation or carbohydrate suggestion. It will be appreciated that the above is a high level description of the device 10, and in practice the device may include additional controls, input ports, output ports, etc., as may be desired to even further enhance the utility of the device 10 or its use with other components and devices (e.g., laptop computers, infusion pumps, etc.). Accordingly, the above description of the device 10 should not be taken as limiting its construction or features in any way.

Figure 2:
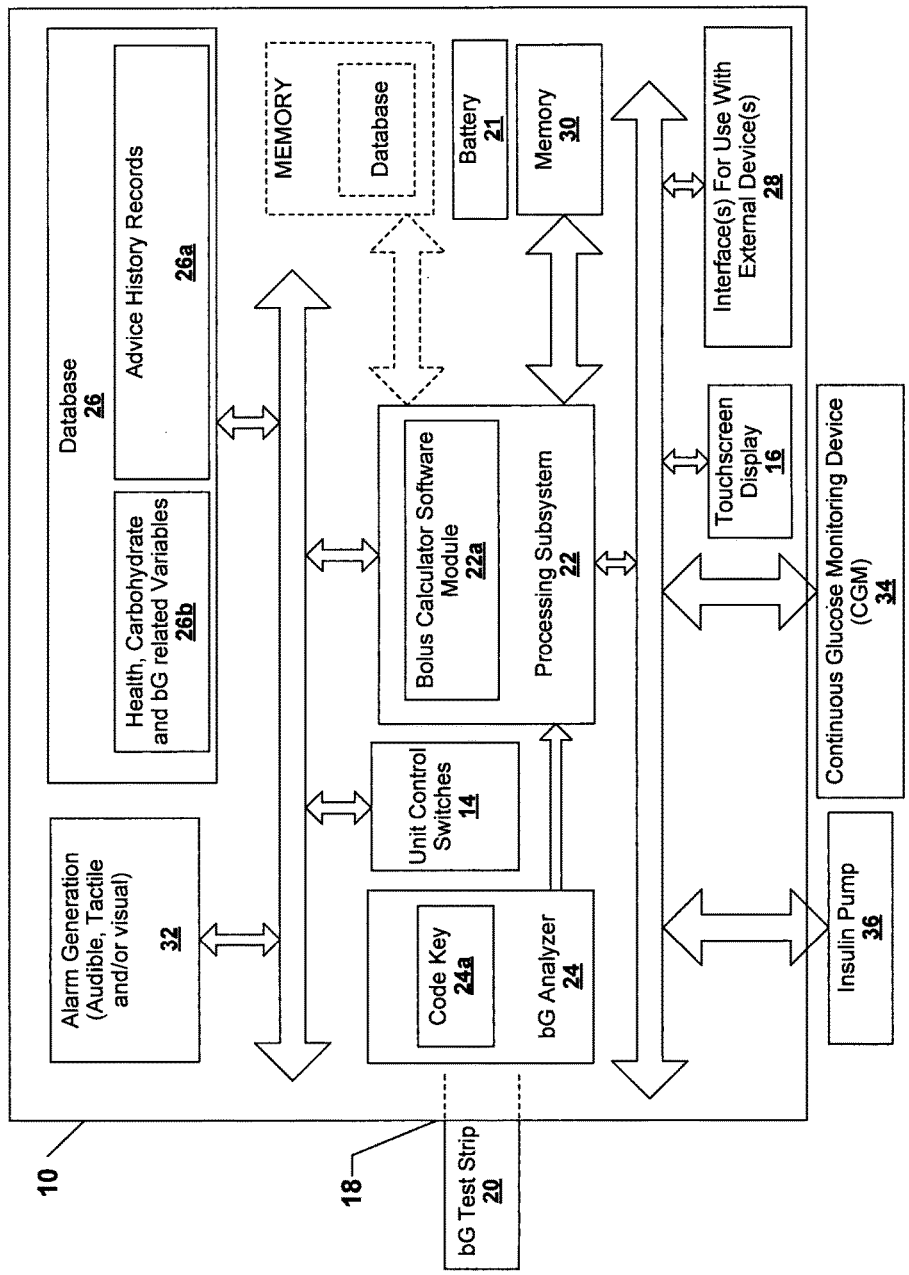
FIG. 2 is a high level block diagram of various components and subsystems that may be incorporated in the device shown in FIG. 1.

Referring to FIG. 2, a high level block diagram of the device 10 is shown. The device 10 can include a rechargeable or non-rechargeable battery 21 for powering the various electronic components of the device 10. A processing subsystem 22 (e.g., a microprocessor based subsystem) is included that receives information from a bG analyzer 24. The bG analyzer 24 is located adjacent the port 18 of the housing 12 to permit the bG analyzer 24 to read the bG test strip 20. The bG analyzer 24 can include a code key 24a that includes calibration information for the bG test strip 20 being read. The processing subsystem 22 can also be in communication with a database 26 that is used to store bG test values obtained from the bG analyzer 24 and other important health related information for the user. In particular, the database 26 can include a subsection 26a for storing recommended bolus and carbohydrate advice history records (hereinafter "advice history records") that are still active in their influence of current and future advice, and a section 26b for storing medication (insulin), health, carbohydrate and bG related variables (e.g., insulin sensitivities of the user for various time segments of the day) pertinent to the user. It will be appreciated that the database 26 will be formed by a non-volatile memory. Further, the bG related variables such as the insulin sensitivities of the user can be stored as global parameters and may not be in the advice history records.

The processing subsystem 22 can also be in communication with the display 16, the user control switches 14, and one or more interfaces 28 for interfacing the device 10 to other external devices. The processing subsystem 22 can also be in communication with a memory (such as a RAM) 30 for storing various types of information (e.g., meal and bed times) that are input by the user, as well as any other information requiring temporary or permanent storage. However, it will be appreciated that the database 26 and the memory 30 could be implemented in a single memory device (e.g., RAM) if desired, as indicated in phantom in FIG. 2. The processing subsystem 22 can be in communication with an alarm generation subsystem 32 that is used to generate an alarm consisting of audible signals, tactile signals (e.g., a vibration signal) or possibly even visual signals such as illuminated lights (e.g., LEDs) on the device 10. The processing subsystem 22 can also receive inputs from a remote continuous glucose monitoring ("CGM") device 34 secured to the user's body such that device 10 is continually updated with glucose information for the user. Finally the processing subsystem 22 can be in communication with a remote insulin infusion pump 36 (herein referred to as an "insulin pump 36") being worn by the user so that the device 10 is able to communicate bolus information to the insulin pump 36. By "remote" it is meant that the CGM device 34 and the insulin pump 36 are each located outside of the device 10 but otherwise still in communication with the device 10. It should be appreciated that the device 10 can communicate with the insulin pump 36 either through a wired or wireless connection.

The device 10 can be used to implement a non-transitory machine readable code, for example a bolus calculator software module 22a (herein referred to as "bolus calculator 22a"), that is run by the processing subsystem 22. The bolus calculator 22a can be formed as a single module or as a collection of independent modules that run concurrently on the processing subsystem 22. The processing subsystem 22, working in connection with the bolus calculator 22a, receives a wide variety of user inputs applied by the user through the touchscreen display 16 to generate a recommended correction bolus, a recommended meal bolus, a recommended total bolus, or when appropriate a suggested carbohydrate amount. The suggested carbohydrate amount may be provided in response to the detection by the device 10 of a hypoglycemic bG test value. The operations and capabilities of the device 10 will be explained in detail in the following paragraphs. The device 10 significantly enhances the convenience and ease of use to the user through the implementation of a plurality of customizable inputs that enable the user to program the device 10 with unique health information pertinent to the user. More specifically, the device 10 allows the user to program the device 10 with health information which even more completely enables the device 10 to take into account unique health conditions affecting the user, as well as regular occurring and non-regular occurring health events that could otherwise have an impact on the bolus and carbohydrate calculations made by the device 10.

In an example embodiment, the bolus calculator 22a is configured to generate advice history records which are indicative of the bolus and carbohydrate calculations and bolus recommendations made by the device 10. The bolus calculator 22a may be further configured to include data indicative of a patient's adherence or variance from the recommendations in the advice history records. In some embodiments, an advice history record can include a plurality of fields, including a time field that defines a time of the advice history record, a test flag field, a record content field indicating one or more types of events defined in the advice history record, and one or more fields defining values corresponding to the events indicated in the record content field.

In an exemplary embodiment, the advice history record includes a time field. The time field denotes a time corresponding to the advice history record. The time can include values indicating a year, a month, a day, an hour, and a minute of the advice history record. It should be appreciated that the time field can be divided into a plurality of subfields for each of the values. When a new advice history record is generated, the time at which the advice history record was generated populates the time field.

In an exemplary embodiment, the test flag field indicates results of one or more tests. The test field may include test flags corresponding to the one or more tests. As should be appreciated, a test flag can be a bit that is set to 1 if the result is true and 0 if the result is false. The test flags can include a HI test flag that indicates whether a bG concentration value is outside of an upper range of values that can be displayed by the device 10. When the HI value is set to 1, the HI test flag indicates that a bG concentration value in above the range of bG concentration values that can be displayed by the device 10. The test flags can further include a LO test flag. When the LO test flag is set to 1, the LO test flag indicates that the bG concentration value is below the range of values that can be displayed by the device 10. The test flags can also include a HYPO test flag. When the HYPO test flag is set to 1, the HYPO test flag indicates that the bG concentration value of the patient corresponds to a hypoglycemic state or is below the lower end of a target range. It is appreciated that the test field may include additional test flags.

As mentioned, the record content field indicates one or more types of events defined in the advice history record or that certain conditions relating to the events were met. The different types of events can include a blood glucose concentration, a carbohydrate amount associated with food intake of the patient, a health percentage value selected by the user, an insulin amount was recommended to the patient, a confirmation that insulin was administered to the patient, a confirmation that a bolus recommendation was accepted by the patient, an indication that a correction bolus was administered, and an indication that a meal bolus was recommended to the patient. As should be appreciated, if one or more events are indicated in the record content field of the advice history record, the corresponding fields in the advice history record are populated with values.

In an exemplary embodiment, the advice history record includes a bG concentration field. The bG concentration field is populated with a valid value when the record content field indicates that a bG concentration value has been associated with the advice history record. The bG concentration value indicates a bG concentration value from a bG measurement performed by the device 10 or was otherwise provided by the patient. It should be appreciated that the bG concentration value can be represented in mg/dL or mmol/L.

In an exemplary embodiment, the advice history record includes a carbohydrate amount field. The carbohydrate amount field is populated with a valid value when the record content field indicates that a carbohydrate amount value has been associated with the advice history record. A carbohydrate amount value is an amount of carbohydrates that a patient consumed in a recent food intake. As will be discussed in further detail below the carbohydrate amount value can be greater than or less than a "snack size" threshold. When the carbohydrate amount value is greater than the "snack size" threshold the food intake is considered a meal as opposed to a snack. The carbohydrate value can be provided by the patient via the user interface of the device 10 and can be represented in grams.

In an exemplary embodiment, the advice history record includes a health percentage amount. The health percentage amount field is populated with a valid value when the record content field indicates that one or more health percentages have been associated with the advice history record. As discussed above, the user can enter different health events, e.g., meals, exercise, periods of stress, and periodic physiological events such as a menstrual cycle. The patient or another user can provide percentages representing an amount of effect that the health event has on increasing or decreasing the bG concentration (or insulin need) of the patient.

In an exemplary embodiment, the advice history record includes a correction bolus field. The correction bolus field is populated with a valid value when the record content field indicates that a non-null correction bolus amount has been associated with the advice history record. The correction bolus amount indicates a bolus amount selected by a patient to either decrease or increase a bG concentration value. A negative bolus amount corresponds to a scenario where the patient's bG concentration is below a target bG value and a positive bolus amount corresponds to a scenario where the patient's bG concentration is above the target bG value. It is noted that in some embodiments, the correction bolus field is populated when the user overrides a correction bolus recommendation provided by the bolus calculator 22a.

In an exemplary embodiment, the advice history record includes a meal bolus field. The meal bolus field is populated with a valid value when the record content field indicates that a non-null meal bolus amount has been associated with the advice history record. The meal bolus amount indicates a bolus amount selected by a patient to either offset the effects of a meal, e.g., carbohydrate intake. In some embodiments, the meal bolus field is populated when the user overrides a meal bolus recommendation provided by the bolus calculator 22a.

In an exemplary embodiment, the advice history record includes a confirmed correction bolus field. The confirmed correction bolus field is populated with a valid value when the record content field indicates that a confirmed insulin amount and a non-null correction bolus amount has been associated with the advice history record. The confirmed correction bolus amount indicates a bolus amount that was delivered to the patient by an insulin pump 36 in response to a patient-saved correction bolus.

In an exemplary embodiment, the advice history record includes a confirmed meal bolus field. The confirmed meal bolus field is populated with a valid value when the record content field indicates that a confirmed insulin amount and a non-null meal bolus amount has been associated with the advice history record. The confirmed meal bolus amount indicates a bolus amount that was delivered to the patient by an insulin pump 36 in response to a patient-saved meal bolus.

It should be appreciated that the advice history record may include variations of the fields described above or alternative or additional fields. The fields of the advice history record provided are provided for example only and not intended to be limiting.

In some embodiments, the advice history record may include one or more different parameter values relating to events defined in the advice history record. For example, the advice history record may include a target value, a meal rise value, an offset time, and an acting time value. The target value is a target bG level of the patient. The target value can be represented as a function of an upper and lower limit for the patient's bG levels. The meal rise value is an amount by which the bG level of a patient may increase with respect to the target value as a result of a carbohydrate intake. In some embodiments, the meal rise value is a function of time and the administration of insulin, such that the meal rise remains constant for a first predetermined amount of time after the patient is administered insulin, i.e., offset time, and then decreases linearly after the first predetermined amount of time. The total amount of time that a dose of insulin has an effect on the bG levels of a patient is the acting time. As will be discussed later, if the meal rise value as a result of the effect of a dose of insulin is graphed, the result is referred to as an action shape. In some embodiments, the action shape is a trapezoid, such that the offset time defines the shorter base and the acting time defines the longer base. Other parameters that may be included in the advice history record may include a carb ratio value, an insulin sensitivity value, and a snack size value. The parameter values may be provided by a user such as the patient or a treating physician of the patient. The parameter values can be uploaded or provided via the touch display 16 of the device 10. The parameter values are utilized by the bolus calculator 22a to determine bolus recommendations for the patient.

Figure 3A:
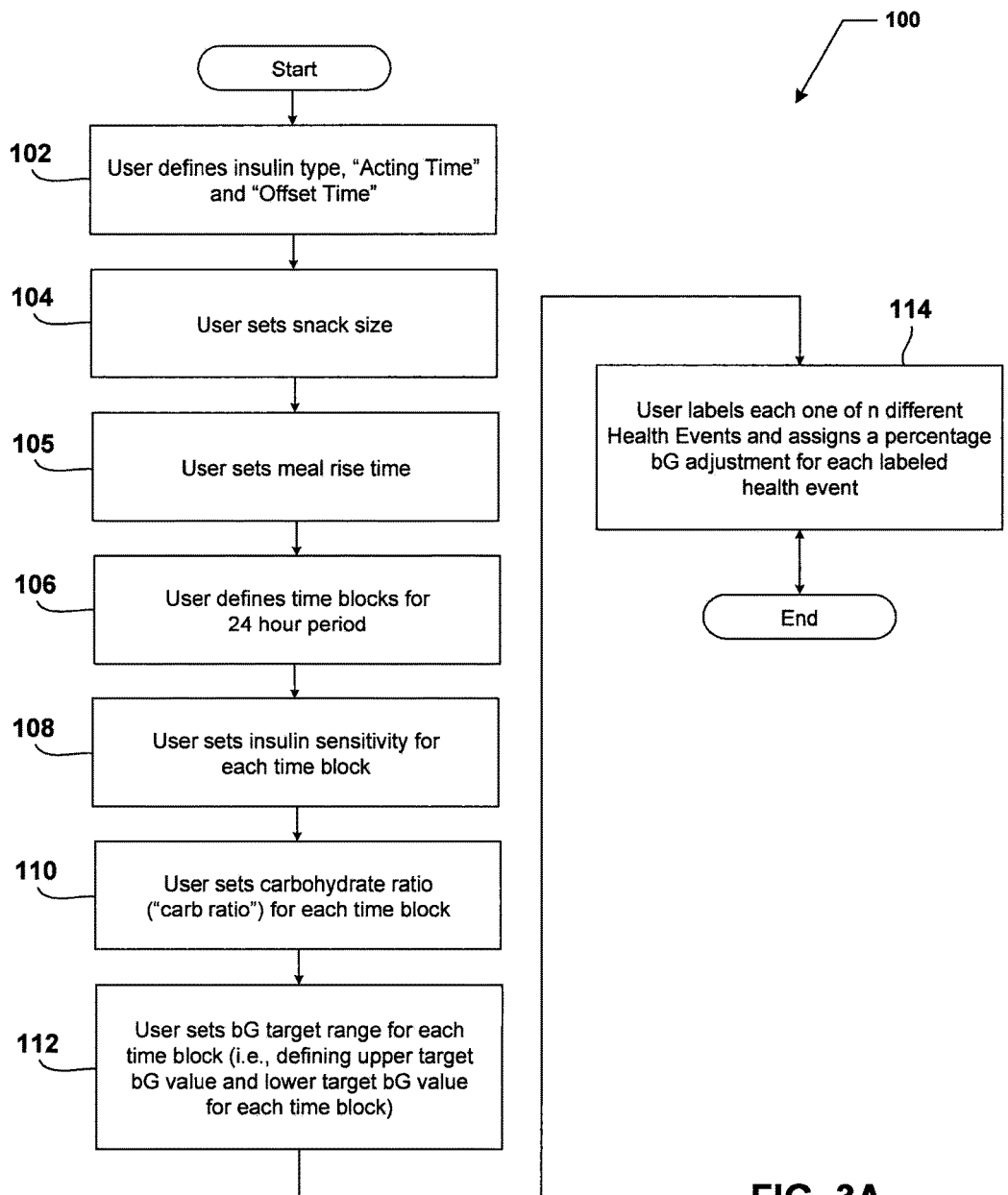
FIG. 3A is an exemplary flowchart illustrating a preliminary configuration procedure for configuring the device shown in FIG. 1.

Referring to FIG. 3A, a flowchart 100 illustrates an exemplary preliminary configuration procedure that the user can perform to configure the various inputs needed to tailor the device 10 to the requirements of the user. At operation 102 the user can define the insulin type that she/he is using, as well as the "acting time" and "offset time" associated with the specified insulin. The user also sets a snack size at operation 104. Any carbohydrate amount greater than the snack size that the user enters into the device 10 will be considered as a "meal" by the device 10 if the amount exceeds the user defined snack size. A meal rise glucose amplitude (expressed in bG units) is also defined by the user at operation 105. At operation 106 the user can define the various time blocks for a twenty four hour period. In one exemplary implementation the user may define up to eight contiguous or non-contiguous time blocks during a twenty four hour period. However, it will be appreciated that a greater or lesser number of time blocks could be provided for. Since the user's insulin sensitivity will be assumed to vary over the course of the day, the user can set a different insulin sensitivity value for each time block, as indicated at operation 108. At operation 110 the user can set a carbohydrate ratio ("carb ratio") for each time block as well, as this ratio can be assumed to vary for different users throughout the course of a day. At operation 112 the user can set a bG target range for each time block, as this range is also presumed to vary slightly over the course of a day. The bG target range is made up of an upper target bG value and a lower target bG value which define the upper and lower bounds, respectively, of the bG target range. It will also be appreciated that the processing subsystem 22 operates to consider an action shape of a previously taken correction bolus, where the action shape is defined by a bG lowering potential of the previously taken correction bolus, as well as the offset time and the acting time of the insulin associated with the previously taken correction bolus. The action shape is considered by the processing subsystem 22 when generating a new bolus recommendation, and will be discussed in greater detail below.

At operation 114 the user labels each one of up to n different health events with a label using the touchscreen display 16 and assigns a percentage bG adjustment for each labeled health event. It is a valuable feature of the device 10 that the user is able to program these various percentage adjustments for each of a plurality of user defined health events that the user knows in advance will affect her/his bG test values. For example, the user may program the device with different bG percentage adjustment values for health events such as "exercise", "illness", "stress", or even for recurring conditions such as a menstrual cycle. The precise percentages selected by the user for each user defined health event can be based on past history and experience of the user or based in part on the advice of a health care professional who is helping the user to manage her/his blood glucose levels. As one example, if the user knows from experience that an exercise event performed right after a meal will reduce a needed meal bolus by about 20%, then the user may enter "−20" in a displayed field on the display 16. The processing subsystem 22 will thereafter use this 20% reduction in calculating the meal bolus and the correction bolus when the exercise event has been selected. These features will be defined in greater detail in the following paragraphs.

Figure 3C:
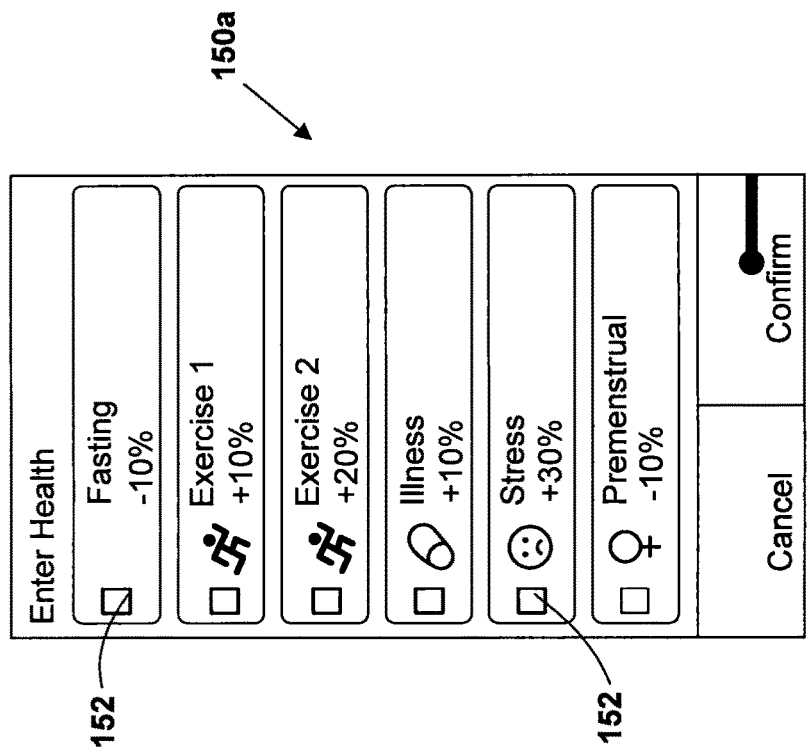
FIG. 3C is an illustration showing how the display of the device may display the various programmed health event options after same are programmed into the device.
Figure 3B:
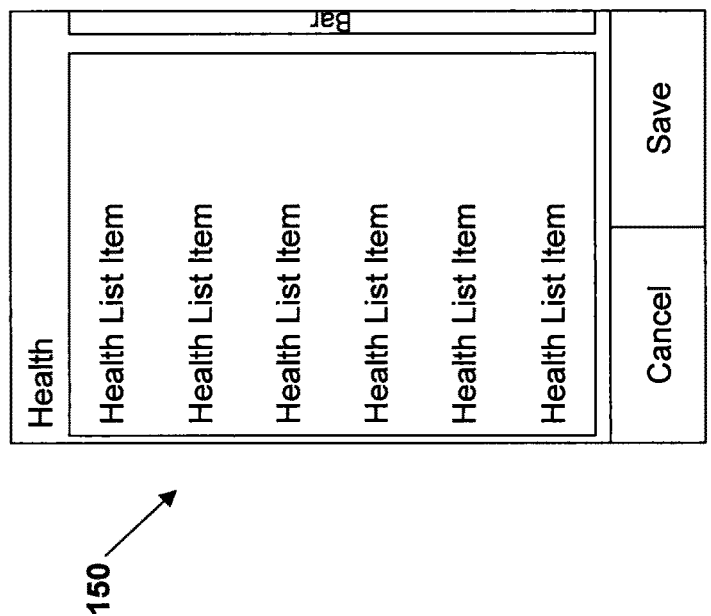
FIG. 3B is a drawing illustrating an example screen for enabling a user to program in various health events to be considered by the device when providing bolus recommendations.
Figure 3E:
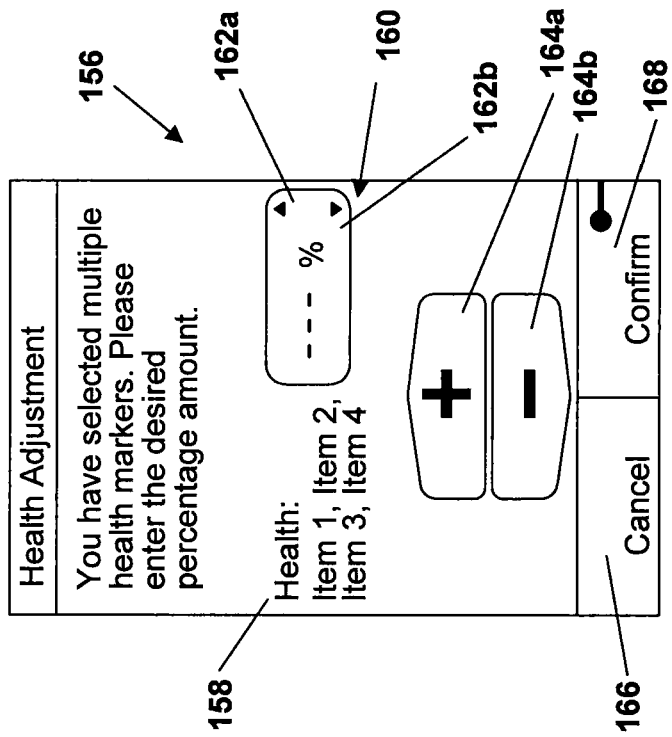
FIG. 3E is an illustration showing how the display of the device may display a message to the user if the user has selected more than one health event, and allows the user to enter a custom health adjustment percentage to be applied to a bolus calculation.
Figure 3D:
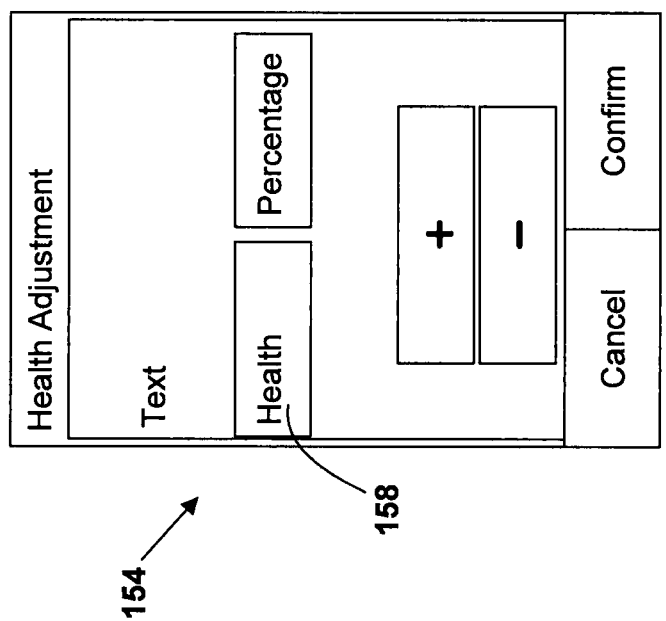
FIG. 3D is a drawing of an exemplary layout that may be presented on the display of the device for allowing the user to enter the percentage adjustment to be made to the health event.
Figure 3F:
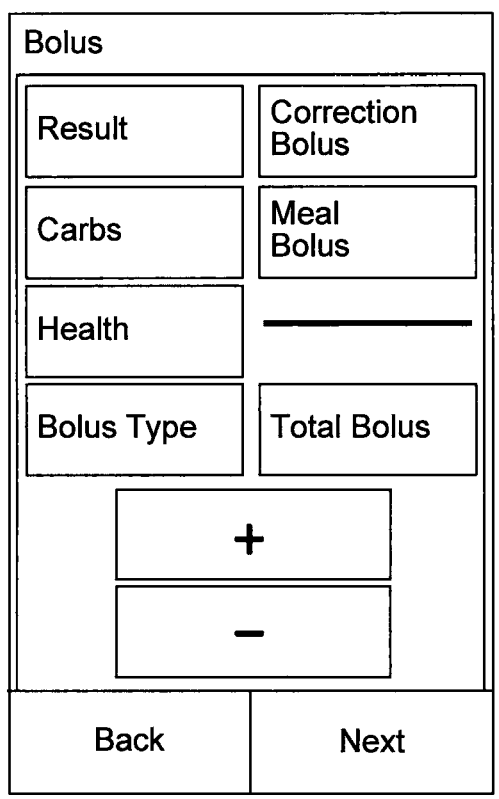
FIG. 3F is a drawing showing an exemplary layout of how various items of information may be presented to the user on the display of the device.

Referring to FIGS. 3B-3F, illustrations are presented of how the various forms of information can be displayed to the user on the display 16 of the device 10. FIG. 3B shows a screen 150 that presents multiple "Health List Item" boxes that may be displayed in the display 16 when the user has chosen to assign a specific health event to a record containing the bG test value that she/he has just obtained. FIG. 3C shows a screen display 150a illustrating how this information can appear on the display 16. The user can select one of the boxes 152 in FIG. 3C, which will mark the just-obtained bG test value with the user programmed specific health event, and thus apply the user programmed percentage adjustment to the just-obtained bG test value. If the user selects two or more health events for a single bG test value, then the device 10 can display a different screen that forces the user to select a "custom" health event percentage that will be applied to the just-obtained bG test value. Such a screen layout 154 is shown in FIG. 3D. An actual exemplary screen display 156 is shown in FIG. 3E that corresponds to the screen layout 154. The "Health" field 158 in FIG. 3E displays all the health events that the user has checked off in boxes 152 of screen display 150a of FIG. 3C. In field 160 the user can enter and/or adjust a custom health percentage adjustment as indicated by the presence of the arrows 162a and 162b. Arrows 164a and 164b may also be displayed, which are used to enable the user to increase or decrease a suggested bolus. User control 166 enables the user to cancel the health event adjustment and control 168 enables the user to confirm the selection (i.e., apply) of the custom health percentage in field 160. FIG. 3F illustrates how various items of information (e.g., result bG test value; carbohydrate information; health adjustment percentage; correction bolus; meal bolus; and total units of recommended bolus) can be displayed to the user on the display 16.

Figure 4A:
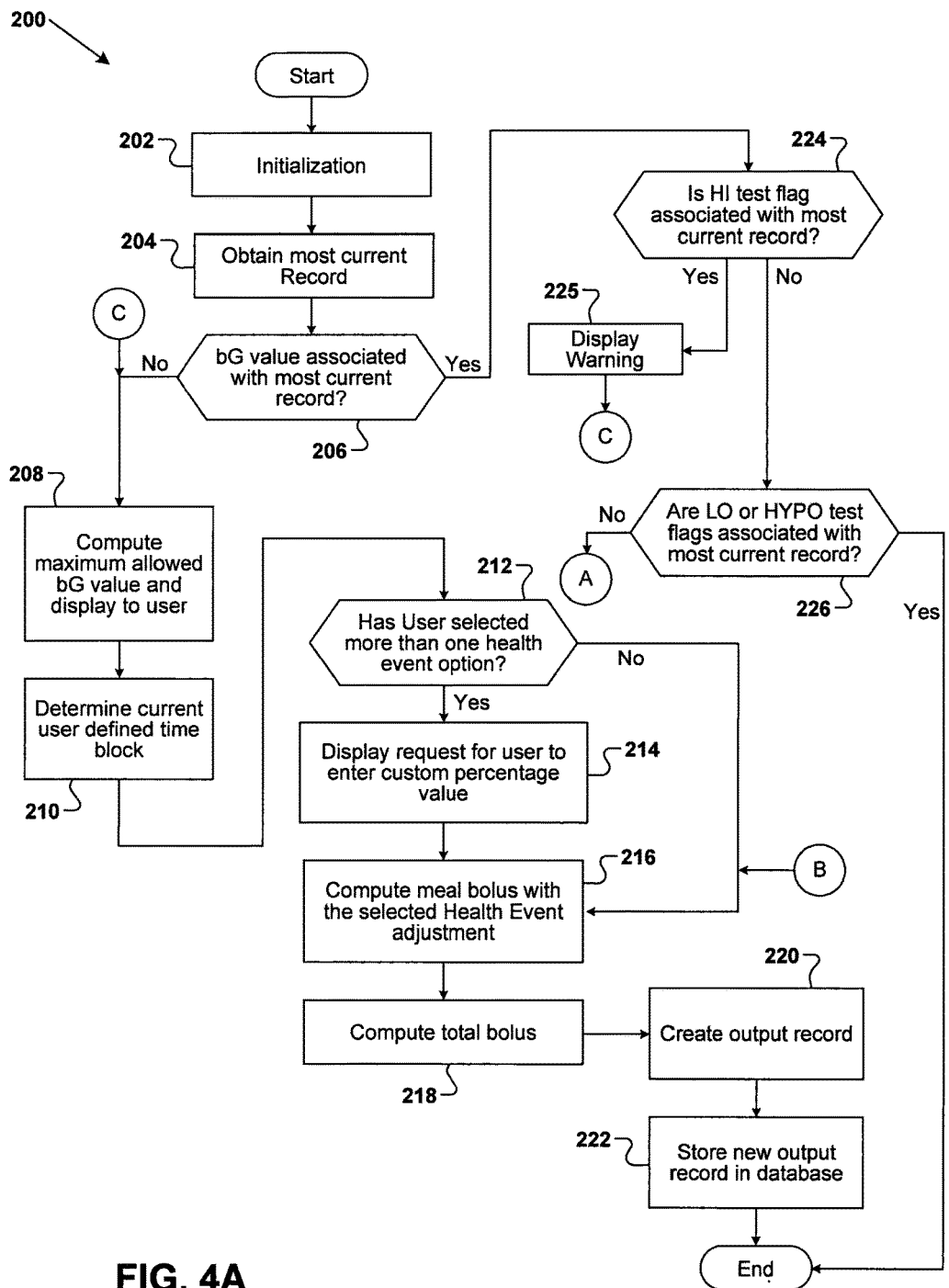
FIGS. 4A and 4B represent an exemplary flowchart illustrating operations that can be performed in computing a total bolus using user defined health adjustment percentages by which the computed meal bolus and computed correction bolus can be modified (by the user) before calculating a recommended total bolus.
Figure 4B:
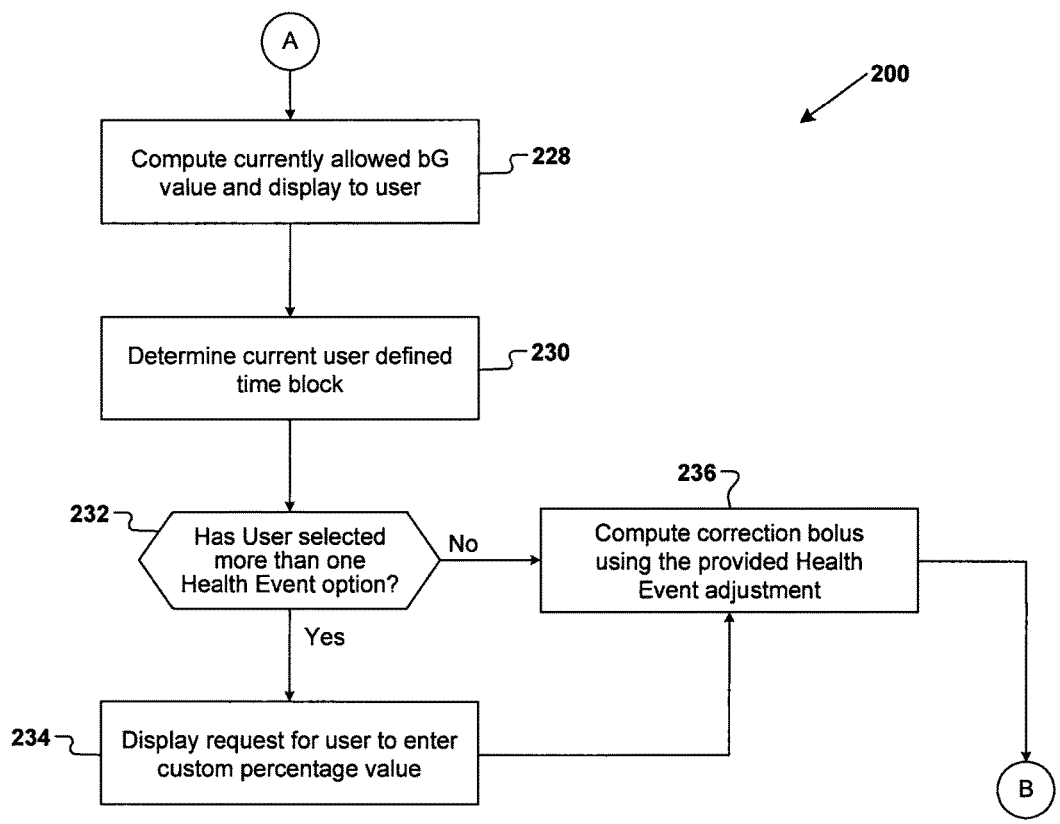

Referring now to FIGS. 4A and 4B, a flowchart 200 is shown of exemplary operations that can be performed by the device 10 in determining a total bolus recommendation for the user that takes into account the configuration programmed into the device 10 by the user. At operation 202 an initialization operation is performed to set the record contents of the processing subsystem 22 to "0". At operation 204 the processing subsystem 22 obtains the most current record stored in the database 26 and checks at operation 206 to determine if it has an associated bG test value. If not, then at operation 208 the maximum allowed bG value is computed and displayed to the user. At operation 210 the processing subsystem 22 determines the current time block. At operation 212 the processing subsystem 22 checks to determine if the user has selected more than one health event option and, if the user has selected more than one option, a request is made on the display 16 for the user to enter a custom percentage value, as indicated at operation 214, that will be applied to subsequent meal bolus and correction bolus calculations. At operation 216 the processing subsystem 22 will compute the meal bolus and apply the selected health event adjustment defined by the user (if any such adjustment has been selected by the user). At operation 218 the processing subsystem 22 will compute the total bolus. At operation 220 the processing subsystem 22 will update and store the output along with the record in the database 26 at operation 222.

Referring further to FIGS. 4A and 4B, if the check at operation 206 reveals that there is a bG value associated with the most current record, then a check is made at operation 224 to see if the "HI" test flag of the record is set, indicating a bG reading that is above a display limit of the device 10, and which therefore will not be used to calculate a recommended correction bolus. If this check provides a "Yes" answer, then after the display of an appropriate warning at operation 225 for a HI bG reading, operations 208-222 may be performed to obtain only a recommendation for a meal bolus. If the check at operation 224 produces a "No" answer, then a check is made to determine if the "LO" or "HYPO" test flags are set for the most current record (Advice Record_IN), as indicated at operation 226. This is an extra check to prevent the recommendation of a bolus in either a hypoglycemic condition or with a bG reading below the display limit of the device 10. In the event of a "Yes" answer, the routine of flowchart 200 ends (and flowchart 300 shown in FIG. 5 begins for calculating a carbohydrate suggestion). If the check at operation 226 produces a "No" answer, then at operation 228 in FIG. 4B the processing subsystem 22 computes the maximum allowed bG value and displays it to the user on the display 16.

Continuing in FIG. 4B, at operation 230 the processing subsystem 22 determines the current user defined time block. At operation 232 the processing subsystem 22 checks to determine if the user has selected more than one health event option and, if the user has selected more than one option, a request is made on the display 16 for the user to enter a custom percentage value, as indicated at operation 234, that will be applied to the correction bolus calculation at operation 236. At operation 236 the processing subsystem 22 will compute the correction bolus and apply the selected health event adjustment defined by the user (if any such adjustment has been selected by the user). Operations 216-222 from FIG. 4A will then be applied. If the check at operation 232 produces a "No" answer, the operation 236 will be performed using the user set health event adjustment.

Figure 5:
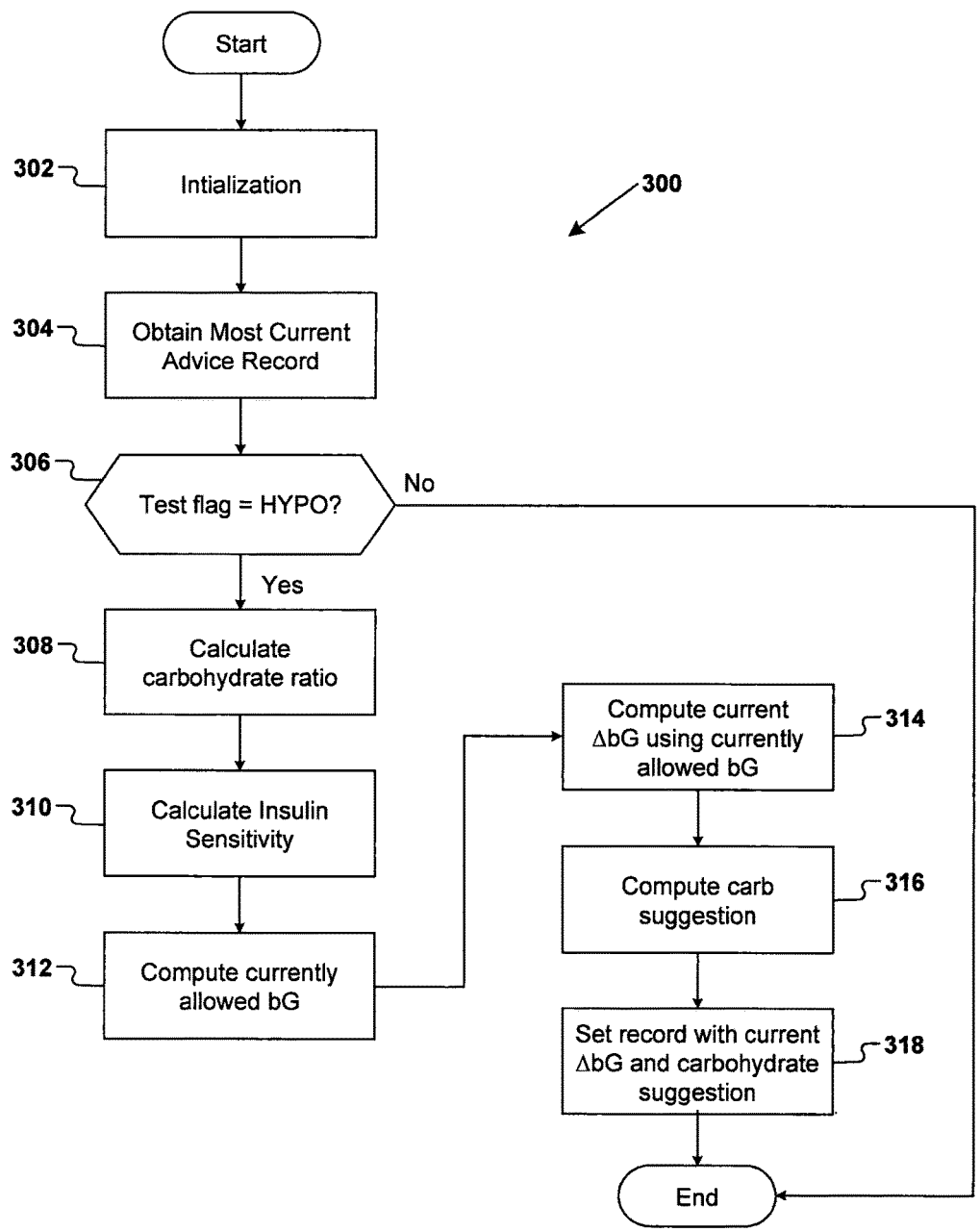
FIG. 5 is an exemplary flowchart illustrating operations that can be performed by the device of FIG. 1 in calculating a carbohydrate suggestion for the user.

Turning to FIG. 5, a flowchart 300 is shown illustrating exemplary operations to show a carbohydrate suggestion can be calculated using the device 10 (this flow occurs based on the "Yes" path at operation 230 in FIG. 4A). At operation 302 an initialization procedure is performed to ensure that any pre-existing data that may be present in the output contents of the processing subsystem 22 is cleared. The most current record is then obtained at operation 304. At operation 306 a check is made to determine if the HYPO test flag of the most current record is set, indicating a hypoglycemic condition for the current bG test value being analyzed. If so, the processing subsystem 22 computes the carbohydrate ("carb") ratio at operation 308 in the traditional manner. At operation 310 the insulin sensitivity is calculated in the traditional manner. At operation 312 the currently allowed bG is computed, which is described in greater detail below. At operation 314 the current delta bG is computed by subtracting the currently allowed bG from the most current record bG concentration. So in effect, operation 314 allows a previously taken correction bolus, which would operate to lower the user's bG, to be factored into the equation for determining the current delta bG. At operation 316 the current delta bG is converted into a carbohydrate suggestion using the insulin sensitivity and by the carbohydrate ratio factors. At operation 318 the outputs of carbohydrate suggestion and current delta bG are stored.

Figure 6:
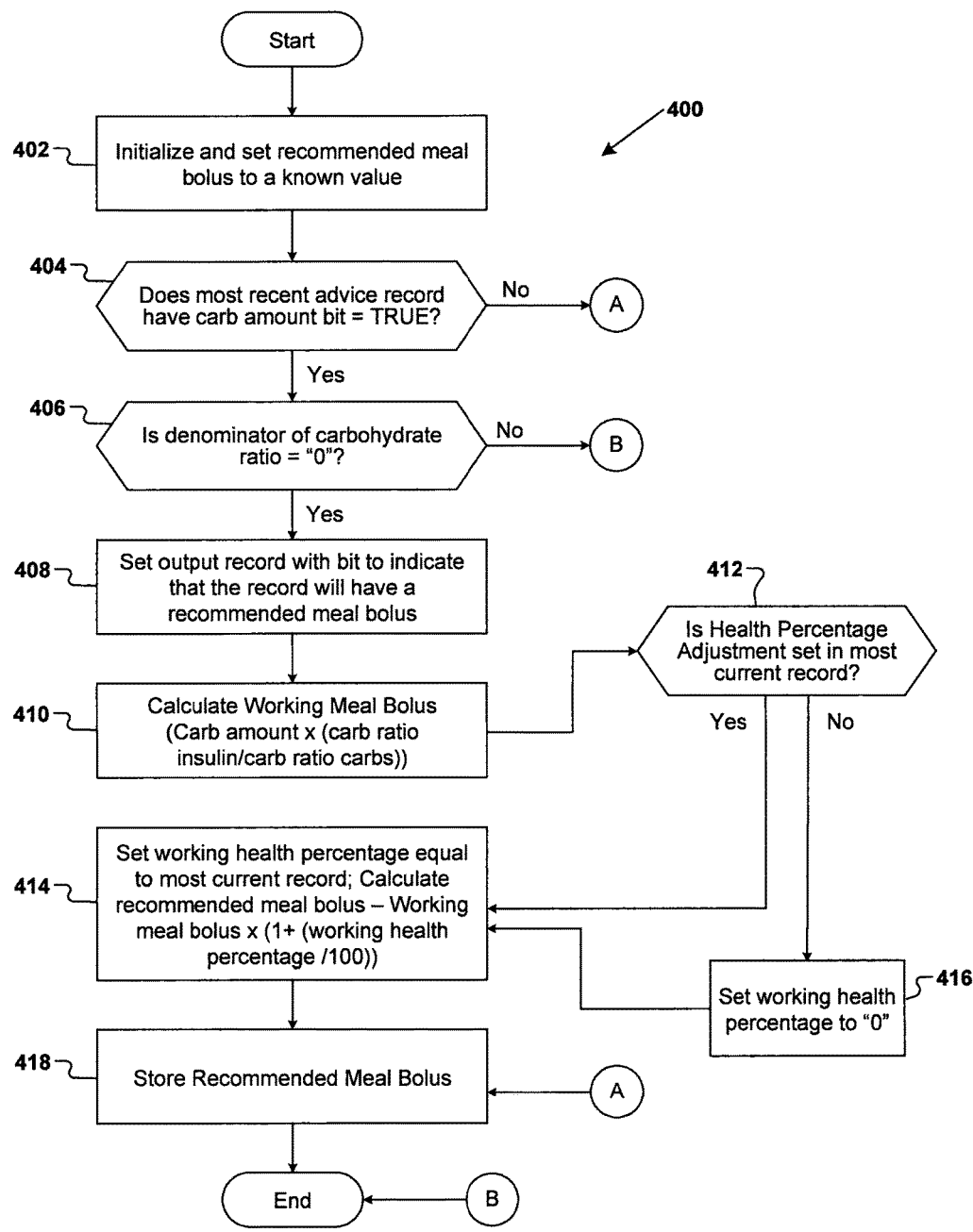
FIG. 6 is a flowchart illustrating exemplary operation performed by the device of FIG. 1 in computing the recommended meal bolus with a user programmed health adjustment applied thereto.

Referring now to FIG. 6, a flowchart 400 is shown illustrating one exemplary manner of computing a meal bolus with a health event adjustment (this flow is called out at operation 216 of FIG. 4B). At operation 402 an initialization is performed to set the recommended meal bolus to a known value. At operation 404 a check is made to determine if the most current record retrieved by the processing subsystem 22 from the database 26 has a carbohydrate amount available for use in the following calculations. If the answer is "Yes", then at operation 406 a check is made to ensure that the denominator of the carbohydrate ratio is not "0". If it is not, then at operation 408 a bit will be set for the output being created by the processing subsystem 22 to indicate a recommended meal bolus is associated with it. At operation 410 the working meal bolus is calculated. At operation 412 a check is made if a health event adjustment percentage is set in the most current record. If so, then at operation 414 a working health percentage is set equal to the health percentage contained in the most current record, and the recommended meal bolus is calculated using this working health percentage. For example, if the user has indicated "−20" in her/his percentage adjustment for the associated health event, then operation 414 uses this information to convert the "−20" to 80%, and the 80% figure is used to modify the working meal bolus to come up with the recommended meal bolus. Thus, in this example the recommended meal bolus would be reduced by 20%. At operation 418 the recommended meal bolus output just created by the processing subsystem 22 is saved in the log records portion 26a of the database 26.

If the check at operation 412 indicates that no health percentage adjustment is indicated in the most current record, then the working health adjustment percentage is set equal to zero at operation 416 and then operations 414 and 418 are repeated. If in operation 404 it is understood that there is no carbohydrate amount from which a recommended meal bolus can be calculated, the recommended meal bolus of zero is simply saved at operation 418. If the denominator of the carbohydrate ratio of the most current record is found to be "0" at operation 406, then the routine ends with an error condition.

Figure 7:
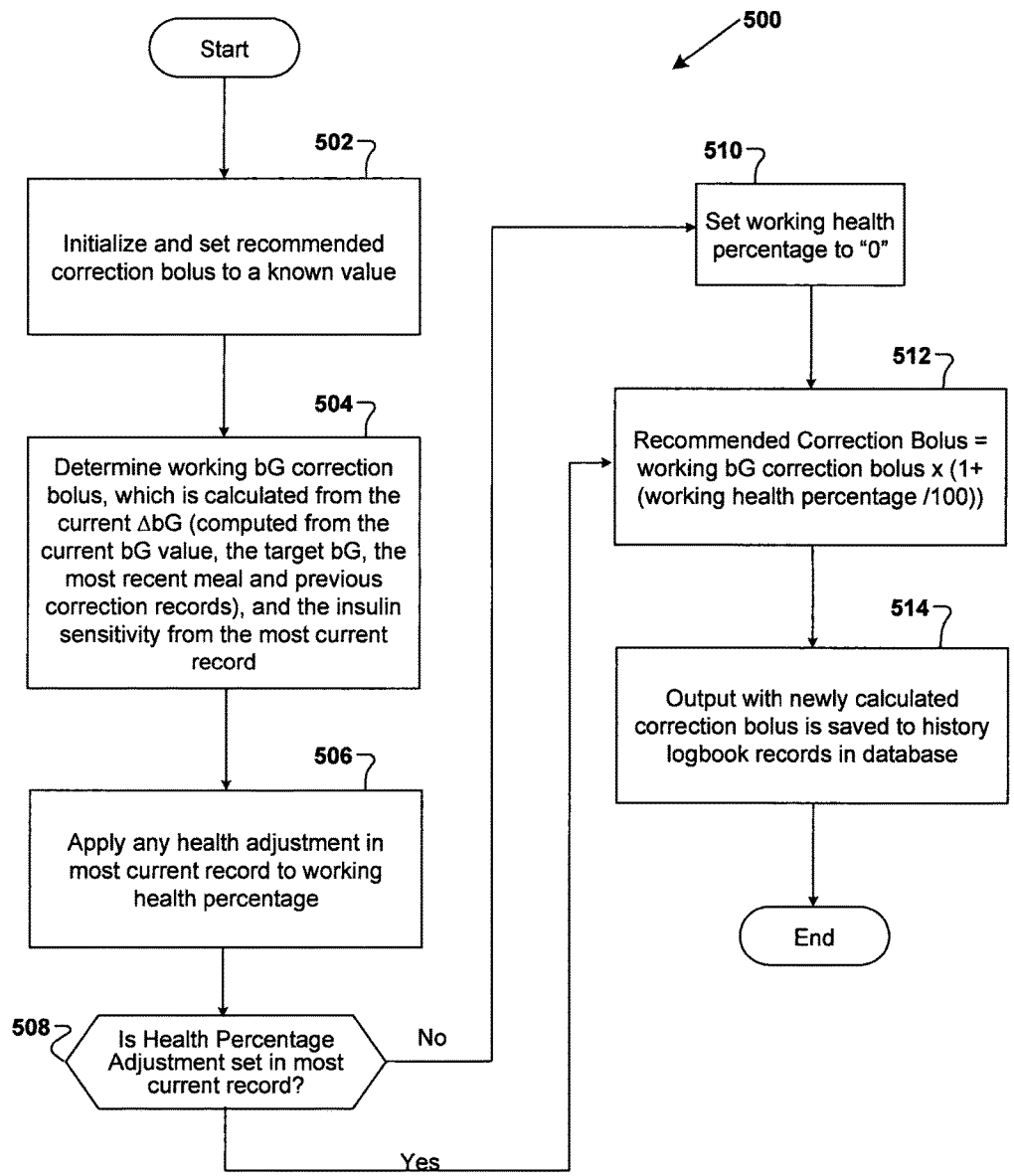
FIG. 7 is a flowchart illustrating exemplary operations that can be performed in computing a recommended correction bolus with a health adjustment percentage set by the user.

Referring to FIG. 7, there is shown an exemplary flowchart 500 setting forth operations that can be performed in computing a correction bolus, taking into account a percentage health adjustment input by the user. It will be appreciated that the operations of flowchart 500 are called by operation 236 in FIG. 4B.

At operation 502 the recommended correction bolus is initialized to a known value. At operation 504 the working bG correction bolus is calculated from the current delta bG (computed from the current bG value, the target bG, the most recent meal and/or previous correction records), and the insulin sensitivity from the most current record. At operation 506 any health adjustment percentage present in the most current record is applied to the working health percentage. Again, if the user has specified "None" when selecting a health adjustment percentage for the bG test value associated with the most current record, then the working health percentage will not be modified by any percentage value, as shown at operation 510. At operation 508 the recommended correction bolus is obtained by modifying the working bG correction bolus by the health percentage adjustment. Thus, if the user had set the health adjustment percentage for the bG test value associated with the most current record to "−25", then the calculation at operation 512 would multiply the working bG correction bolus by 75%. The output with the newly calculated recommended correction bolus is then saved to the database history logbook records 26a at operation 514.

In calculating the correction delta bG, an advantage of the device 10 is that the working delta bG is allowed to be a negative value. This allows a portion of any correction to be removed from the newly calculated correction delta bG, such as if the user had previously taken some carbohydrates to compensate for a LO or HYPO bG value, to be factored into the newly calculated correction delta bG. Another advantage is that for computing a carbohydrate suggestion for the user, the recommendations can be calculated to the currently allowed bG value rather than to the center of the bG target range.

Figure 8:
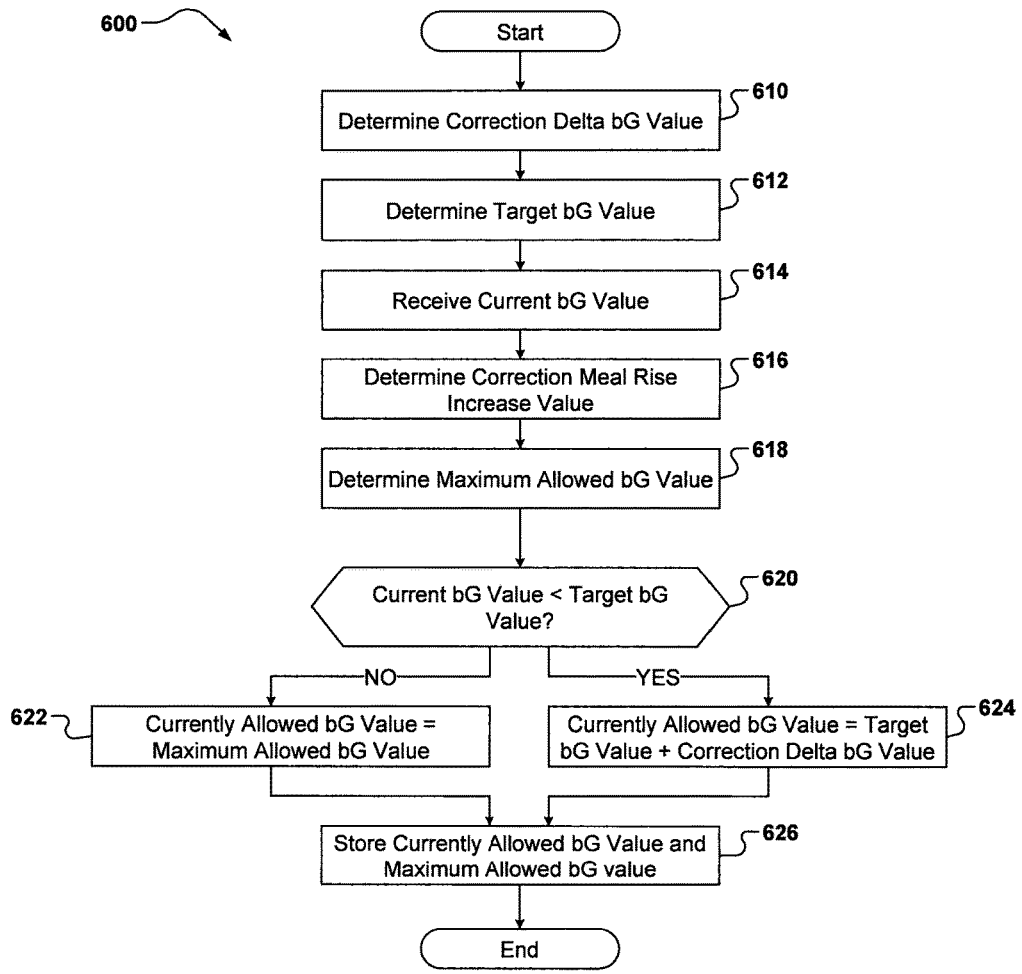
FIG. 8 is a flowchart illustrating exemplary operations that can be performed by the device of FIG. 1 in computing a currently allowed bG value.

As was discussed with respect to FIG. 5, a currently allowed bG value is computed at operation 312. Similarly, a currently allowed bG value is computed at operation 504 of FIG. 7. In some embodiments, the bolus calculator 22a computes the currently allowed bG value based on whether the current bG measurement of the patient is less than the target bG value of the patient. FIG. 8 illustrates an example method 600 for computing the currently allowed bG value. The currently allowed bG value is indicative of a value that a patient's bG value may increase to at a current time without requiring correction bolus. As should be appreciated the method 600 may be executed by the processing subsystem 22 of the device 10 and in particular, can be implemented as part of the bolus calculator 22a. For purposes of explanation, the method 600 is explained as being performed by the bolus calculator 22a.

At operation 610, the bolus calculator 22a computes a correction delta bG value. The correction delta bG value is indicative of an aggregated bG lowering effect of the events defined in the one or more active advice history records of the patient. An example method for determining the correction delta bG value is described in further detail below and with respect to FIG. 9.

At operation 612, the bolus calculator 22a computes a target bG value. In some embodiments, the target bG value is determined as an average of the upper target bG value and the lower target bG value. The upper target bG value and the lower target bG value can be provided to the device 10 by the patient or another user such as the treating physician. Further, the upper target bG value and lower target bG value may be stored in the advice history records. Alternatively, the target bG value can be manually entered by a user.

At operation 614, the bolus calculator 22a receives the current bG measurement value. As discussed above, the current bG measurement value can be determined when the patient provides a blood sample and the blood sample is analyzed by the device 10.

At operation 616, the bolus calculator 22a determines a correction meal rise value based on a specific advice history record of the plurality of advice history records. As will be discussed below, the specific advice history record that is used can include: i) an event corresponding to the patient eating a meal that is greater than a snack size, ii) an event corresponding to a meal bolus amount, and iii) an event corresponding to the patient or an insulin pump 36 verifying that insulin was actually administered to the patient. The correction meal rise value indicates an amount the bG level of the patient can increase as a result of a meal eaten by the patient and with respect to the target bG value without requiring an additional correction bolus. An example technique for determining the correction meal rise value is discussed in greater detail below and with respect to FIG. 10.

At operation 618, the bolus calculator 22a determines a maximum allowed bG value. The maximum allowed bG value indicates the maximum value for the patient's bG measurement before recommending a correction bolus to the patient. In some embodiments, the maximum bG value can be determined by summing the target bG value, the correction delta bG value, and the correction meal rise value.

At operation 620, the bolus calculator 22a compares the current bG measurement value with the target bG value. If the bolus calculator 22a determines that the current bG measurement value is greater than the target bG value, the bolus calculator sets the currently allowed bG value equal to the maximum allowed bG value, as shown at operation 622. If the bolus calculator 22a determines that the current bG measurement value is less than the target value, the bolus calculator 22a sets the currently allowed bG value equal to the sum of the target bG value and the correction delta bG value, as shown at operation 624. At operation 626, the bolus calculator 22a stores the currently allowed bG value and maximum allowed bG value.

It should be appreciated that the exemplary method 600 is provided for example only. Variations of the method 600 are contemplated and are within the scope of the disclosure. Further, the ordering of the operations are not intended to be limiting and different orderings are contemplated and within the scope of the disclosure.

Figure 9:
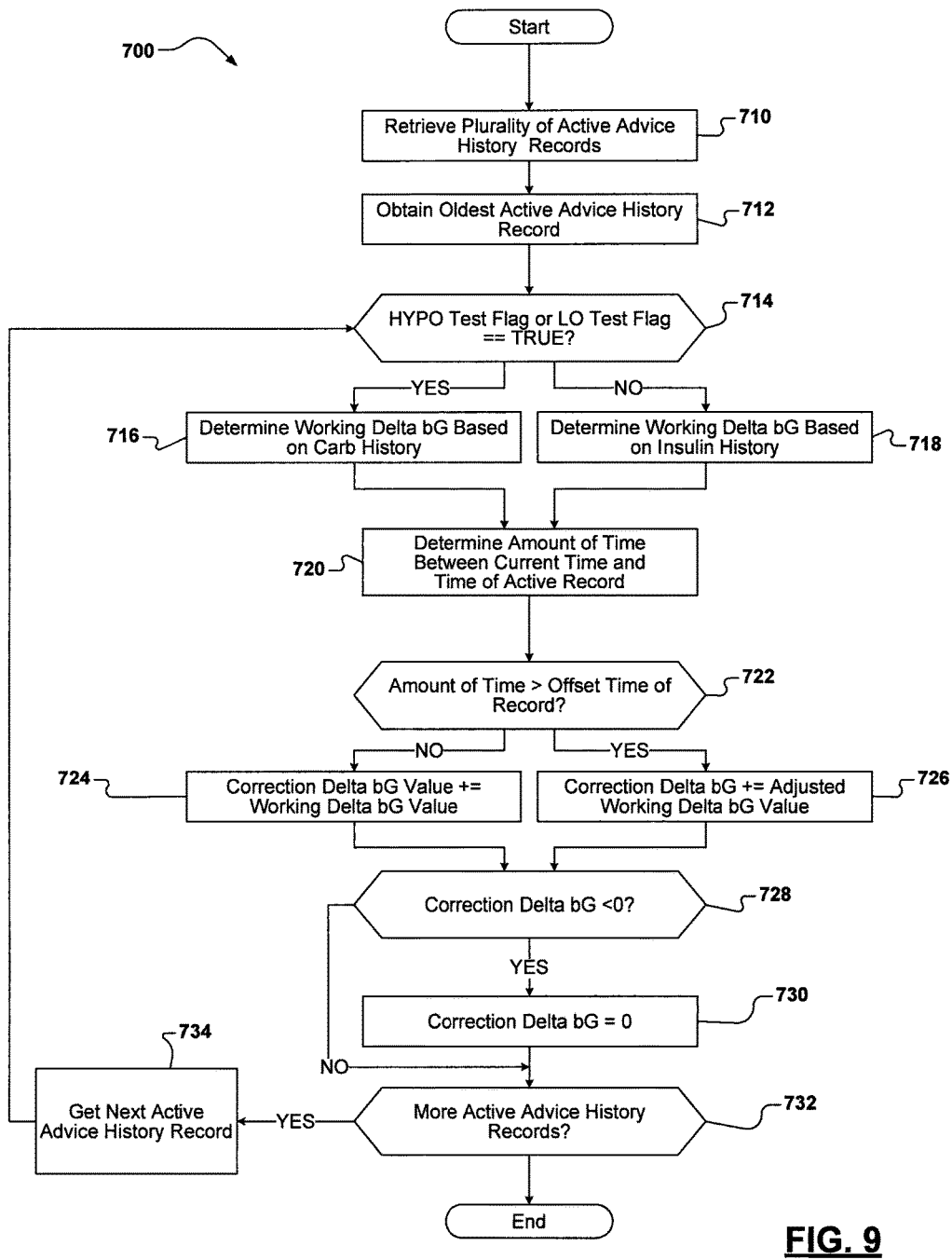
FIG. 9 is a flowchart illustrating exemplary operations that can be performed by the device of FIG. 1 in computing a correction delta bG value.

As was previously discussed, the bolus calculator 22a determines a correction delta bG value. The correction delta bG value indicates an aggregated bG lowering effect of the events defined in the advice history records. Put another way, the correction delta bG value indicates the overall lowering effect of the insulin that is still active in the patient's body. In some embodiments, the bolus calculator 22a analyzes the active advice history records from the oldest active advice history record to the most recent active advice history record to determine the aggregated bG lowering effect of the events defined therein. FIG. 9 illustrates an exemplary method 700 for determining the correction delta bG value. For purposes of explanation, the method 700 is described as being performed by the bolus calculator 22a.

At operation 710, the bolus calculator 22a retrieves the plurality of active advice history records. As previously described, the plurality of active advice history records are the advice history records defining events that are still affecting the patient's bG levels. For example, if an event defined in an advice history record is a correction bolus that was administered three hours prior to the current time and the active time of the insulin dose was three or more hours, the advice history record would be included in the plurality of active advice history records. Conversely, an advice history record corresponding to 48 hours prior to the current time, the advice history record would not be included in the plurality of active advice history records. At operation 712, the bolus calculator 22a selects the oldest advice history record of the plurality of active advice history records.

At operation 714, the bolus calculator 22a determines whether either of the HYPO test flag or the LO test flag in the selected advice history record is set to 1. If so, the bolus calculator 22a determines a working delta bG value based on a carbohydrate intake of the patient defined in the advice history record, as shown at operation 716. If neither the HYPO test flag or the LO test flag are set to 1 in the selected advice history record, the bolus calculator 22a determines the working delta bG value based on an insulin that was administered to the patient at a time corresponding to the selected active history record, as shown at operation 718. The working delta bG value is the amount by which the patient's bG level is currently decreased or increased by as a result of the events defined in the selected advice history record.

At operation 720, the bolus calculator 22a determines the amount of time that has lapsed since the selected advice history record was generated. As discussed, the advice history record includes a time corresponding to the advice history record. The bolus calculator 22a utilizes the time defined in the advice history record to determine the amount of time that has lapsed since the advice history record was generated.

At operation 722, the bolus calculator 22a determines whether the amount of time that has lapsed since the advice history record was generated is greater than the offset time defined in the advice history record. If the amount of time is less than the offset time, then the bolus calculator 22a increments the correction delta bG value by the full amount of the working delta bG value, as shown at operation 724. If the amount of time is greater than the offset time, the bolus calculator 22a increments the correction delta bG value by the result of a predetermined formula, as shown at operation 726. For example, in some embodiments the correction delta bG value is incremented by the amount:

$$\frac{WorkingDeltabG}{Acting\_Time - Offset\_Time} \times (Acting\_Time - Time)$$

Where Acting_Time is the duration during which events defined in the selected advice history record effects the bG level of a patient, Offset_Time is the duration during which the full effect of events defined in the selected advice history record apply, and Time is the difference between the current time and the time when the advice history record was generated. As should be appreciated, the differences in time, e.g., Acting_Time-Offset_Time and Acting_Time-Time may be represented in minutes or seconds. Furthermore, Acting_Time and Offset_Time may be defined in the selected active history record.

At operation 728, the bolus calculator 22a compares the running total of the correction delta bG value to a predetermined threshold, e.g., 0. As should be appreciated, the bolus calculator 22a aggregates the total effect of bG influencing events defined in the plurality of active advice history records to calculate the correction delta bG. At each iteration, e.g., after analyzing another active advice history record, if the running total is less than 0, the bolus calculator 22a sets the running total for the correction delta bG to 0 at operation 730. Otherwise, the running total for the correction delta bG is not altered.

At operation 732, the bolus calculator 22a determines whether there are any remaining active advice history records remaining in the plurality of active advice history records left to analyze. If so, the bolus calculator 22a obtains the next advice history record, as shown at operation 734, and repeats the operations described above. Else, the bolus calculator 22a stops the routine and stores the aggregated correction delta bG value.

It is appreciated that the foregoing method 700 is provided for example only and not intended to be limiting. Other techniques for determining the correction delta bG value are contemplated and are within the scope of the disclosure.

Figure 10:
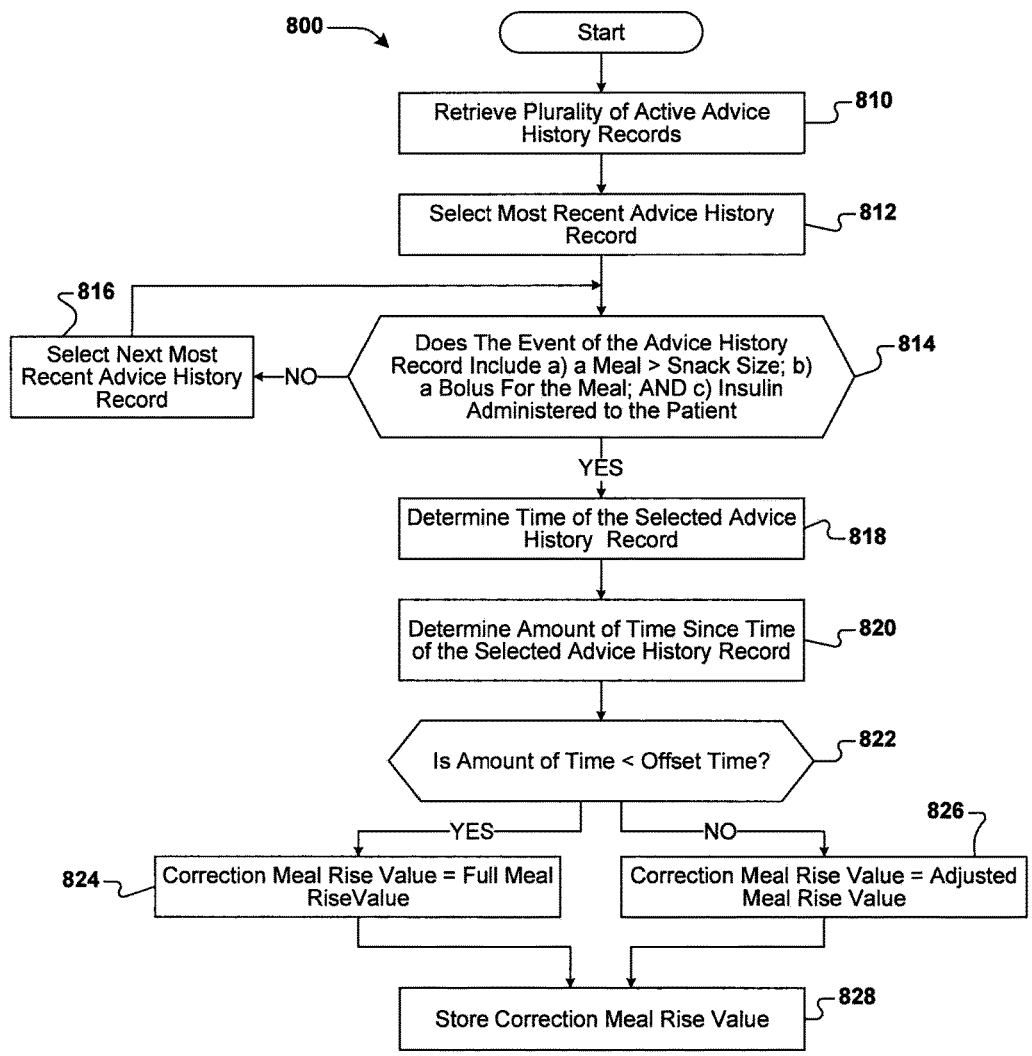
FIG. 10 is a flowchart illustrating exemplary operations that can be performed by the device of FIG. 1 in computing a correction meal rise value.

As described above, the bolus calculator 22a is configured to determine a correction meal rise value, which is indicative of an amount the bG level of the patient can increase with respect to the target bG value without requiring a meal bolus. In some embodiments, the bolus calculator 22a analyzes the active advice history records to select the most recent relevant active advice history record. Using the selected active advice history record, the bolus calculator 22a determines the amount of time that has lapsed since the record was generated to determine the correction meal rise value. FIG. 10 illustrates an example method 800 for determining a correction meal rise value. For purposes of explanation, the method 800 is explained as being executed by the bolus calculator 22a.

At operation 810, the bolus calculator 22a obtains the plurality of active advice history records. As described previously, the plurality of active advice history records are the advice history records that were generated within an acting time. That is, the events defined in the advice history record may be still influencing the bG measurements of a patient. At operation 812, the bolus calculator 22a selects the most recent advice history record.

At operation 814, the bolus calculator 22a analyzes the selected advice history record to determine whether the advice history record includes: i) an event corresponding to the patient eating a meal that is greater than a snack size, ii) an event corresponding to a meal bolus amount, and iii) an event corresponding to the patient or an insulin pump 36 verifying that insulin was actually administered to the patient.

If one or more of the conditions are not met, the bolus calculator 22a obtains the next most recent advice history record, as shown at operation 816. If all of the above-identified conditions are met, the bolus calculator 22a determines the time of the selected advice history record, as shown at operation 818. It is noted that if the bolus calculator 22a cannot identify a record meeting the above-stated criteria, the method ends and the meal rise value is set equal to 0.

At operation 820, the bolus calculator 22a determines the amount of time that has lapsed since the selected advice history record was generated. At operation 822, the bolus calculator 22a determines whether the amount of time that has lapsed is less than the offset time defined in the selected advice history record. If the amount of time is less than the offset time, the correction meal rise value is set equal to the full amount of the meal rise value, as indicated in the action shape defining meal rise values, as shown at operation 824. As discussed, the values of the action shape may be entered by a user such as the patient or a treating physician. If, however the amount of time is greater than the offset time, the bolus calculator 22*a* sets the correction meal rise value equal to an adjusted meal rise value, as shown at 826. In some embodiments, the bolus calculator 22*a* sets the correction meal rise value equal to the result of a predetermined formula, as shown at 826. For example, the adjusted meal rise value can be set equal to the result of the following formula:

$$\frac{Meal\_Rise}{Acting\_Time - Offset\_Time} \times (Acting\_Time - Time)$$

where Meal_Rise is the full meal rise value defined in the action shape corresponding to the selected advice history record, Acting_Time is the duration during which the selected advice history record effect the bG level of a patient, Offset_Time is the duration during which the full effect of the events defined in the selected advice history record apply, and Time is the amount of time since the selected advice history record was generated. Acting_Time and Offset_Time may be defined in the selected active history record. At operation 828, the correction meal rise value is stored.

It is appreciated that the foregoing method 800 is provided for example only and not intended to be limiting. Other techniques for determining the correction meal rise value are contemplated and are within the scope of the disclosure.

Figure 11A:
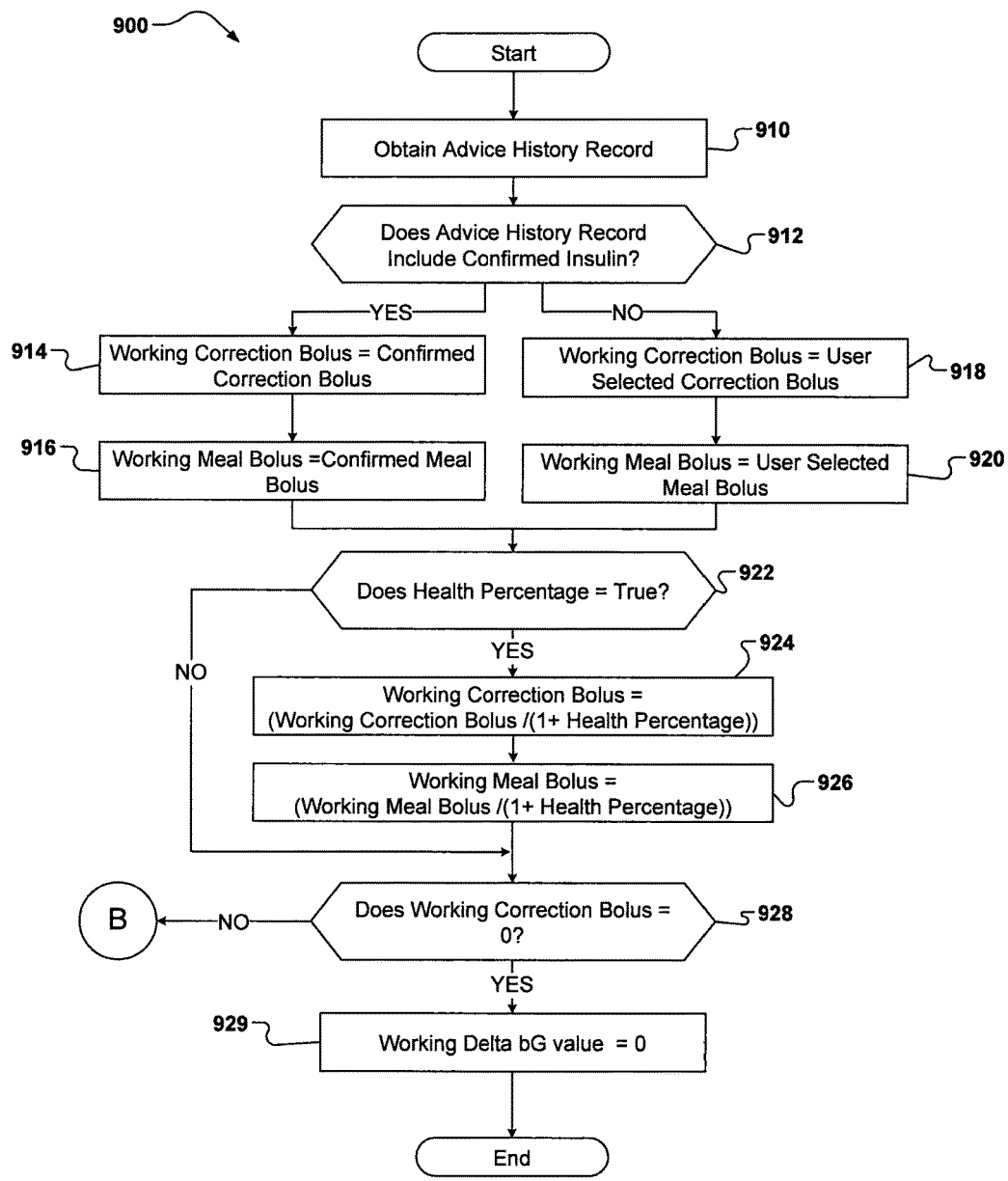
FIGS. 11A and 11B are flowcharts illustrating exemplary operations that can be performed by the device of FIG. 1 in computing a working delta bG value based on an insulin history of the patient.
Figure 11B:
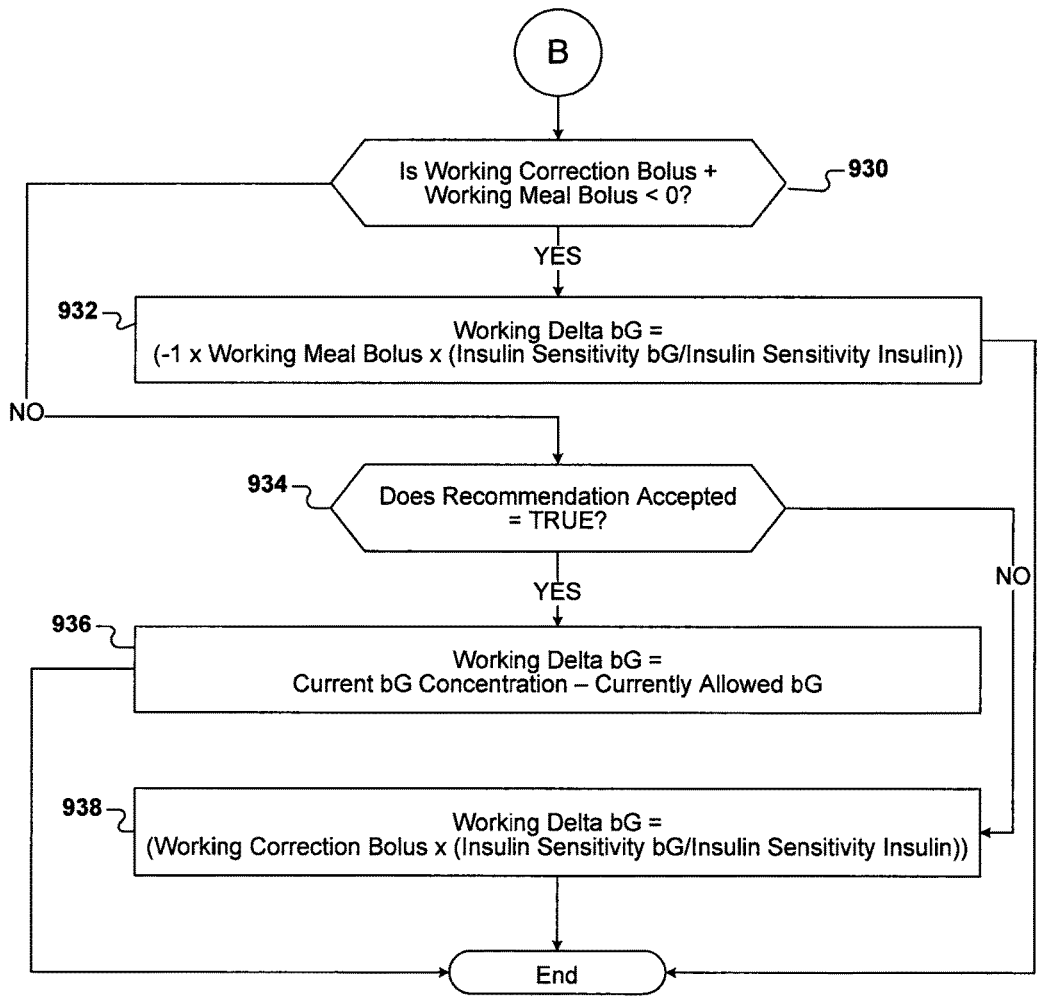

As previously discussed with respect to FIG. 9, when the bolus calculator 22*a* is determining the working correction delta bG value for a particular advice history record, the bolus calculator 22*a* determines whether the HYPO or LO test flag is set to true. If neither flag is set, the bolus calculator determines the working delta bG value based on the insulin history of the patient. FIGS. 11A and 11B together illustrate an example method 900 for determining the working delta bG value based on the insulin history the patient.

At operation 910, the bolus calculator 22*a* obtains the advice history record for which the working correction delta bG value is being calculated. At operation 912, the bolus calculator 22*a* determines whether the events defined in the advice history record include a confirmation that insulin was administered to the patient by an insulin pump 36. If so, a working correction bolus value is set equal to the confirmed correction bolus value identified in the advice history record and a working meal bolus value is set equal to the confirmed meal bolus value identified in the advice history record, as shown at operations 914 and 916, respectively. If there was no confirmed insulin defined in the advice history record, the bolus calculator 22*a* sets the working correction bolus value equal to the user selected correction bolus value identified in the advice history record and the working meal bolus value equal to the user selected meal bolus value, as shown at operations 918 and 920, respectively.

At operation 922, the bolus calculator 22*a* determines whether the health percentage value defined in the advice history record is defined. If a health percentage value is defined, the working correction bolus is set equal to:

$$\left(\frac{WorkingCorrectionBolus}{1 + HealthPercentage}\right)$$

where WorkingCorrectionBolus is the working correction bolus value as determined above and HealthPercentage is the health percentage value defined in the advice history record, as shown at operation 924. It is appreciated that the health percentage value can be a decimal representation of the percentage. Further, at operation 926, the working meal correction bolus value is set equal to:

$$\left(\frac{WorkingMealBolus}{1 + HealthPercentage}\right)$$

where WorkingMealBolus is the working correction bolus value determined above. It is appreciated that the health percentage value can be a decimal representation of the percentage. If at operation 922, a health percentage is not defined, the working correction bolus and the working meal bolus values are left unchanged.

At operation 928, the bolus calculator 22*a* determines whether the working correction bG value is equal to 0. If so, the bolus calculator 22*a* sets the working delta bG value equal to 0, as shown at operation 929, and the process returns the working delta bG value.

If the working correction bG value is not equal to 0, the bolus calculator 22*a* determines whether the sum of the working correction bolus value and the working meal bolus value is less than 0, as shown at operation 930. If so, the bolus calculator 22*a*, as shown at operation 932, calculates the working delta bG value according to:

Working_Delta_bG_value =

$$-1 \times WorkingMealBolus \times \left(\frac{InsulinSensitivitybG}{InsulinSensitivityInsulin}\right)$$

where WorkingMealBolus is the working meal bolus value determined above, and InsulinSensitivitybG and InsulinSensitivityInsulin are predetermined values provided by the patient or another user in the advice history record. Once the working delta bG value is determined the method 900 ends.

If, however, the sum of the working correction bolus value and the working meal bolus value is not less than 0, the bolus calculator 22*a* determines whether the patient had accepted the bolus recommendation identified in the advice history record, as shown at operation 934. If so, at operation 936 the bolus calculator 22*a* determines the working delta bG value according to:

Working_Delta_bG_value=bG_Concentration−Currently_Allowed_bG where bG_Concentration is the measured bG concentration value identified in the advice history record and the Currently_Allowed_bG is the currently allowed bG value in the advice history record, the calculation of which was described in greater detail above. If the advice history record does not indicate that the bolus recommendation was accepted, at operation 938 the bolus calculator 22*a* determines the working delta bG value according to:

$$\text{Working\_Delta\_bG\_value} =$$
$$\text{WorkingCorrectionBolus} \times \left( \frac{\text{InsulinSensitivitybG}}{\text{InsulinSensitivityInsulin}} \right)$$

where WorkingCorrectionBolus is the working correction bolus value, described above, and InsulinSensitivitybG and InsulinSensitivityInsulin are predetermined values provided by the patient or another user in the advice history record. Once the working delta bG value is determined, the working delta bG value is returned and the method 900 stops executing.

It is appreciated that the foregoing method 900 is provided for example only and not intended to be limiting. Other techniques for determining the working delta bG value are contemplated and are within the scope of the disclosure.

Figure 12:
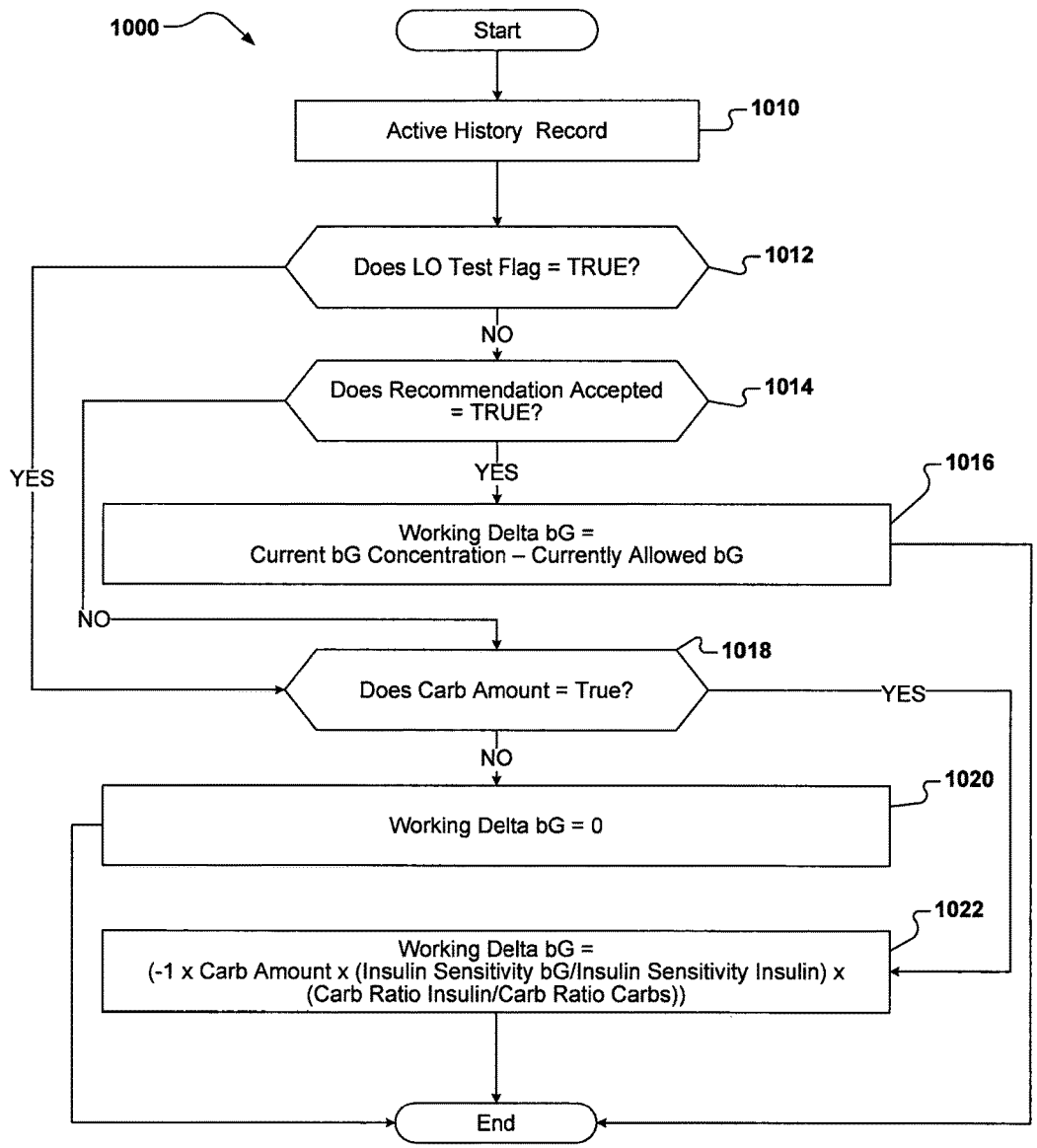
FIG. 12 is a flowchart illustrating exemplary operations that can be performed by the device of FIG. 1 in computing a working delta bG value based on a carbohydrate history of the patient.

As previously discussed with respect to FIG. 9, when the bolus calculator 22a is determining the working correction delta bG value for a particular advice history record, the bolus calculator 22a determines whether the HYPO or LO test flag is set to true. If one or both flags are set, the bolus calculator 22a determines the working delta bG value based on the carbohydrate history of the patient. FIG. 12 illustrates an example method 1000 for determining the working delta bG value based on the carbohydrate history the patient.

At operation 1010, the bolus calculator 22a receives the advice history record for which the working correction delta bG value is being calculated. At operation 1012, the bolus calculator 22a determines whether the LO test flag is set. If the LO test flag is not set, at operation 1014 the bolus calculator 22a determines whether the bolus recommendation indicated in the advice history record was accepted. If the bolus recommendation was accepted, at operation 1016 the bolus calculator 22a determines the working delta bG value according to the following:

Working_Delta_bG_value=bG_Concentration−Currently_Allowed_bG where bG_Concentration is the measured bG concentration value identified in the advice history record and the Currently_Allowed_bG is the currently allowed bG value in the advice history record.

If the advice history record indicates that the LO test flag was true or the bolus recommendation was not accepted, the bolus calculator 22a determines whether a carbohydrate amount value as associated with the advice history record, as shown at operation 1018. If not, the working delta bG value is set equal to 0, as shown at operation 1020. If a carbohydrate value was associated with the advice history record, at operation 1022 the bolus calculator 22a calculates the working delta bG value according to:

$$\text{Working\_Delta\_bG\_value} =$$
$$-1 \times \text{CarbAmount} \times \left( \frac{\text{InsulinSensitibitybG}}{\text{InsulinSensitivityInsulin}} \right) \times \left( \frac{\text{CarbRatioInsulin}}{\text{CarbRatioCarbs}} \right)$$

where CarbAmount is the carbohydrate amount value associated with the advice history record and InsulinSensitivitybG, InsulinSensitivityInsulin, CarbRatioInsulin and CarbRatioCarbs are predetermined values provided by the patient or another user in the advice history record. Once the working delta bG value is determined, the working delta bG value is returned and the method 1000 stops executing.

It is appreciated that the foregoing method 1000 is provided for example only and not intended to be limiting. Other techniques for determining the working delta bG value are contemplated and are within the scope of the disclosure.

Figure 13A:
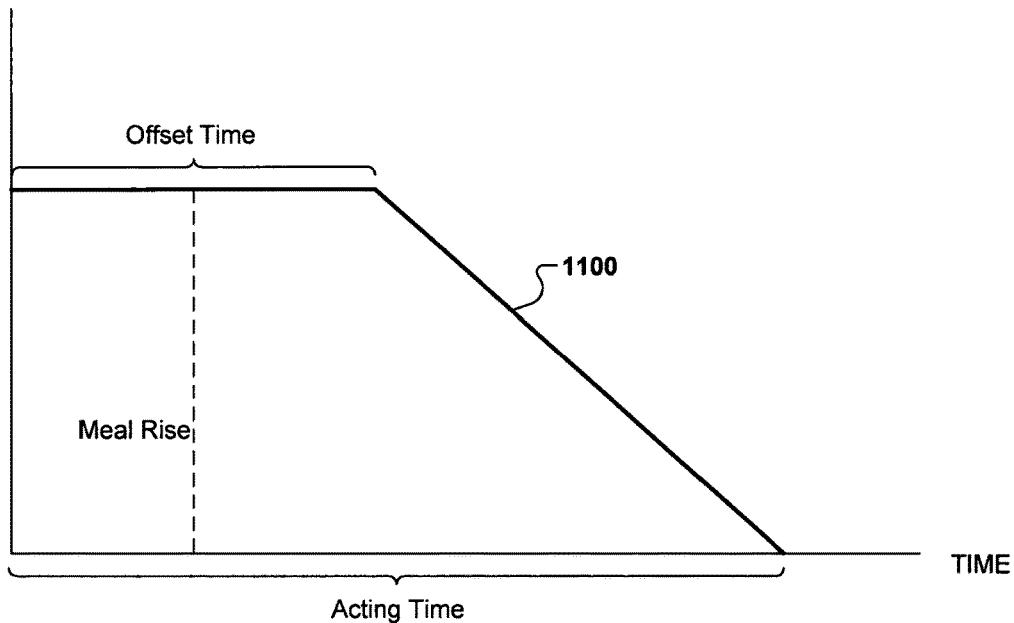
FIGS. 13A and 13B are drawings illustrating an example of a lag time being incorporated to an action shape.
Figure 13B:
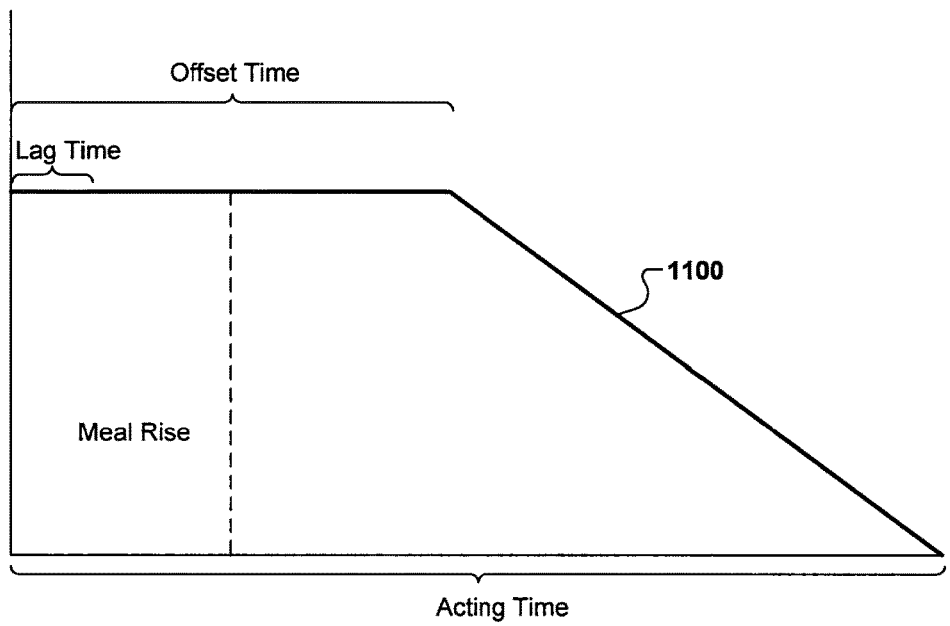

In some embodiments, the patient can provide an indication to the bolus calculator 22a that a dose of insulin will be administered in the near future, e.g., in about 10 minutes. In these embodiments, the bolus calculator 22a can adjust the offset time in the advice history record to compensate for the lag time that will result from the later administered insulin. FIGS. 13A and 13B illustrate an example of lag time being compensated for in such a situation. In FIG. 13A, an action shape 1100 is illustrated. The action shape 1100 of FIG. 13A presumes that the patient will administer insulin at the time of the bolus recommendation. If, however, the patient provides an indication that the insulin will be administered shortly thereafter, the bolus calculator 22a can adjust the offset time and acting time defined in the action shape to account for the lag time between the bolus recommendation and when the insulin will be administered. FIG. 13B illustrates an example of the action shape 1100 after the lag time is accounted for. As should be appreciated, the offset time and the acting time have both been increased by the lag time.

In some embodiments, the patient can turn a bolus advice feature on or off. When the bolus advice feature is turned off, the bolus calculator 22a may be configured not to generate advice history records for various events. If, however, the patient decides to turn the bolus advice feature on, the bolus calculator 22a may require previous advice history records to perform the methods described above. Thus, in some embodiments, when the patient turns the bolus advice feature on, the bolus calculator 22a creates a plurality of advice history records and back-fills the parameter values described above with the values provided by the user, e.g., the patient or the patient's physician. In these embodiments, the various fields may be left empty as the particular data, e.g., bG measurement values and meal histories, to fill the values may not have been recorded. If, however, the data was maintained, the data may be automatically back-filled into the advice history records as well.

In some embodiments, the patient can provide instructions to the insulin pump 36 to deliver a bolus. The user has the option to manually deliver the bolus. When the bolus is administered, the bolus calculator 22a includes the amount of bolus delivered to the patient. A situation may arise however, where the patient is provided with a bolus recommendation, including a recommended amount of insulin, but manually delivers a bolus amount that does not match the recommended amount of insulin. This may be because the patient was unable to enter the precise amount using the user interface of the insulin pump 36 or because of a partial delivery error by the pump. Thus, in some embodiments, the bolus calculator 22a is configured to compare the amount manually entered by the patient as the bolus amount delivered to the bolus recommendation amount. If there is a discrepancy, the bolus calculator 22a determines whether the discrepancy was due to the patient being unable to enter the exact amount using the user interface of the insulin pump 36, e.g., if the amount entered is within a "step-size" of the bolus recommendation. If this is the case, the bolus calculator 22a stores the recommendation accepted as "TRUE" (for example in operation 934). If, however, the amount entered is much greater or much less than the bolus recommendation, the bolus calculator 22a stores the recommendation accepted as "FALSE" and acts on the amount of insulin manually entered by the patient.

What is claimed is:

1. A computer-implemented method for determining an allowable amount of blood glucose (bG) of a patient, the allowable amount of blood glucose being used to calculate a bolus recommendation for a patient, the method comprising:

maintaining a plurality of active advice history records in a data store of a computing device, each of the plurality of active advice history records having been generated during a predetermined time period relative to a current time, and each of the plurality of active advice history records identifying data relating to one or more bG influencing events and including a time corresponding to the one or more bG influencing events;

measuring, by a sensor of the computing device, a current bG measurement corresponding to the patient, the current bG measurement indicating a current bG level of the patient;

determining, by one or more processors of the computing device, a target bG value for the patient, the target bG value corresponding to a desired bG level for the patient;

determining, at the one or more processors, a correction delta bG value based on one or more records of the plurality of active advice history records, the correction delta bG value being indicative of an aggregated bG lowering effect of the events defined in the one or more active advice history records on a bG value of the patient;

determining, at the one or more processors, a correction meal rise value based on a specific active advice history record of the plurality of active advice history records, the correction meal rise value being indicative of an amount the bG level of the patient can increase with respect to the target bG value without requiring a correction bolus;

determining, at the one or more processors, a maximum allowed bG value based on the target bG value, the correction delta bG value, and the correction meal rise value;

comparing, at the one or more processors, the current bG measurement to the target bG value;

setting, at the one or more processors, the allowable amount of bG value equal to the maximum allowed bG value when the current bG measurement is greater than the target bG value;

setting, at the one or more processors, the allowable amount of bG value using the target bG value and the correction delta bG value and excluding the correction meal rise value when the current bG measurement is less than the target bG value;

storing the allowable amount of bG value in the data store of the computing device;

calculating, at the one or more processors, a recommendation for the patient using the allowable amount of bG value; and presenting the recommendation to the patient on a display of the computing device.

2. The method of claim 1, wherein when the current bG measurement is less than the target bG value, the allowable amount of bG value is set equal to the sum of the target bG value and the correction delta bG value.

3. The method of claim 1, wherein determining the correction delta bG value further comprises:

for each active advice history record of the plurality of active advice history records:

analyzing the active advice history record to determine a bG lowering effect associated with the active advice history record; and aggregating the bG lowering effect associated with previous bG lowering effects corresponding to previously analyzed active advice history records, wherein the correction delta bG value is determined based on the aggregation of the bG lowering effect of all of the plurality of active advice history records.

4. The method of claim 3, wherein determining the correction delta bG value further comprises:

for each active advice history record of the plurality of active advice history records:

after aggregating the bG lowering effect associated with the previous bG lowering effects corresponding to the previously analyzed active history records, determining whether the aggregated bG lowering effect is less than zero; and when the aggregated bG lowering effect is less than zero, setting the aggregated bG lowering effect equal to zero, wherein the correction delta bG value is determined based on the aggregation of the bG lowering effect of all of the plurality of active advice history records and the active advice history records are analyzed sequentially beginning with an oldest active advice history record.

5. The method of claim 3, wherein analyzing the active advice history record further comprises:

determining whether a bG measurement defined in the active advice history record is below a bG threshold;

when the bG measurement defined in the active history record is less than the bG threshold, determining the bG lowering effect associated with the active advice history record based on a carbohydrate amount defined in the active advice history record; and when the bG measurement defined in the active history record is greater than the bG threshold, determining the bG lowering effect associated with the active advice history record based on an insulin amount defined in the active advice history record.

6. The method of claim 3, wherein analyzing the active advice history record further comprises:

determining an amount of time that that has lapsed since the active advice history record was generated;

comparing the amount of time to an offset time associated with the active advice history record, the offset time indicating a first duration during which the events defined in the active advice history record have a full effect on the bG level of the patient;

when the amount of time is greater than the offset time, adjusting the bG lowering effect associated with the active advice history record based on:

$$\frac{WorkingDeltabG}{\text{Acting\_Time} - \text{Offset\_Time}} \times (\text{Acting\_Time} - \text{Time})$$

where WorkingDeltabG is the bG lowering effect associated with the active advice history record, Acting_Time is a second duration during which the events defined in the active advice history records effect the bG level of a patient, Offset_Time is the offset time, and Time is the amount of time.

7. The method of claim 1, wherein determining the correction meal rise value comprises ensuring the events defined in the specific active advice history record include a bolus being associated with a carbohydrate intake event where the carbohydrate intake is greater than a predetermined threshold and further include an indication that insulin was administered to the patient and correspond to a time that is temporally closer to a current time than other active advice history records in the plurality of active advice history records defining events that include a meal bolus and a confirmation of insulin.

8. The method of claim 1, wherein determining the correction meal rise value further comprises:
determining an amount of time that has lapsed since the time corresponding to the specific active advice history record;
comparing the amount of time to a predetermined threshold associated with the specific active advice history record;
when the amount of time is less than the predetermined threshold, setting the correction meal rise value equal to a full meal rise value defined in the specific active advice history record; and
when the amount of time is greater than the predetermined threshold, setting the correction meal rise value equal to an adjusted meal rise value based on the amount of time and the full meal rise value.

9. The method of claim 8, wherein the adjusted meal rise value is determined according to:

$$\frac{\text{Meal\_Rise}}{\text{Acting\_Time} - \text{Offset\_Time}} \times (\text{Acting\_Time} - \text{Time})$$

where Meal_Rise is the full meal rise value associated with the specific active advice history record, Offset_Time is a first duration during which the events defined in the specific active advice history record have a full effect on the bG level of the patient, Acting_Time is a second duration during which the events defined in the specific active advice history records effect the bG level of a patient, and Time is the amount of time.

10. A diabetes management device configured to determine an allowable amount of blood glucose (bG) of a patient, the allowable amount of blood glucose being used to calculate a bolus recommendation for a patient, the device comprising:
an advice history records database that stores a plurality of active advice history records, each of the plurality of active advice history records having been generated during a predetermined time period relative to a current time, and each of the plurality of active advice history records identifying data relating to one or more bG influencing events and including a time corresponding to the one or more bG influencing events;
a computer-readable medium storing computer-readable instructions;
one or more processors configured to execute the computer-readable instructions, the computer-readable instructions, when executed by the one or more processors, causing the one or more processors to:
receive a current bG measurement corresponding to the patient, the current bG measurement indicating a current bG level of the patient;
determine a target bG value for the patient, the target bG value corresponding to a desired bG level for the patient;
determine a correction delta bG value based on one or more records of the plurality of active advice history records, the correction delta bG value being indicative of an aggregated bG lowering effect of the events defined in the one or more active advice history records on a bG value of the patient;
determine a correction meal rise value based on a specific active advice history record of the plurality of active advice history records, the correction meal rise value being indicative of an amount the bG level of the patient can increase with respect to the target bG value without requiring a correction bolus;
determine, a maximum allowed bG value based on the target bG value, the correction delta bG value, and the correction meal rise value;
compare the current bG measurement to the target bG value;
set the allowable amount of bG value equal to the maximum allowed bG value when the current bG measurement is greater than the target bG value;
determine the allowable amount of bG value using the target bG value and the correction delta bG value and excluding the correction meal rise value when the current bG measurement is less than the target bG value; and
store the allowable amount of bG value.

11. The device of claim 10, wherein the computer readable instructions, when executed by the one or more processors, cause the one or more processors to set the allowable amount of bG value equal to the sum of the target bG value and the correction delta bG value when the current bG measurement is less than the target bG value.

12. The device of claim 10, wherein the computer readable instructions, when executed by the one or more processors, further cause the one or more processors to:
for each active advice history record of the plurality of active advice history records:
analyze the active advice history record to determine a bG lowering effect associated with the active advice history record; and
aggregate the bG lowering effect associated with previous bG lowering effects corresponding to previously analyzed active advice history records,
wherein the correction delta bG value is determined based on the aggregation of the bG lowering effect of all of the plurality of active advice history records and the active advice history records are analyzed sequentially beginning with an oldest active advice history record.

13. The device of claim 12, wherein the computer readable instructions, when executed by the one or more processors, further cause the one or more processors to:
for each active advice history record of the plurality of active advice history records:
after aggregating the bG lowering effect associated with the previous bG lowering effects corresponding to the previously analyzed active history records, determine whether the aggregated bG lowering effect is less than zero; and
set the aggregated bG lowering effect equal to zero when the aggregated bG lowering effect is less than zero.

14. The device of claim 12, wherein the computer readable instructions, when executed by the one or more processors, further cause the one or more processors to:
determine whether a bG measurement defined in the active advice history record is below a bG threshold;
determine the bG lowering effect associated with the active advice history record based on a carbohydrate amount defined in the active advice history record when the bG measurement defined in the active history record is less than the bG threshold; and determine the bG lowering effect associated with the active advice history record based on an insulin amount defined in the active advice history record when the bG measurement defined in the active history record is greater than the bG threshold.

15. The device of claim 12, wherein the computer readable instructions, when executed by the one or more processors, further cause the one or more processors to:

determine an amount of time that that has lapsed since the active advice history record was generated;

compare the amount of time to an offset time associated with the active advice history record, the offset time indicating a first duration during which the events in the active advice history record have a full effect on the bG level of the patient;

when the amount of time is greater than the offset time, adjust the bG lowering effect associated with the active advice history record based on:

$$\frac{WorkingDeltabG}{Acting\_Time - Offset\_Time} \times (Acting\_Time - Time)$$

where WorkingDeltabG is the bG lowering effect associated with the active advice history record, Acting_Time is a second duration during which the events defined in the active advice history records effect the bG level of a patient, Offset_Time is the offset time, and Time is the amount of time.

16. The device of claim 10 wherein determining the correction meal rise value further comprises ensuring the events defined in the specific active advice history record include a bolus being associated with a carbohydrate intake event where the carbohydrate intake is greater than a predetermined threshold and further include an indication that insulin was administered to the patient and correspond to a time that is more recent to a current time than other active advice history records in the plurality of active advice history records defining events that include a meal bolus and a confirmation of insulin.

17. The device of claim 10, wherein the computer readable instructions, when executed by the one or more processors, further cause the one or more processors to:

determine an amount of time that has lapsed since the time corresponding to the specific active advice history record;

compare the amount of time to an offset time associated with the specific active advice history record;

set the correction meal rise value equal to a full meal rise value defined in the specific active advice history record when the amount of time is less than the offset time; and when the amount of time is greater than the offset time, set the correction meal rise value equal to:

$$\frac{Meal\_Rise}{Acting\_Time - Offset\_Time} \times (Acting\_Time - Time)$$

where Meal_Rise is the full meal rise value associated with the specific active advice history record, Offset_Time is a first duration during which the events defined in the specific active advice history record have a full effect on the bG level of the patient, Acting_Time is a second duration during which the events defined in the specific active advice history records effect the bG level of a patient, and Time is the amount of time.

18. The device of claim 10 further comprises a bG analyzer configured to receive a test strip and operates to determine the current bG measurement from a sample of blood on the test strip.

19. The device of claim 10 wherein the computer readable instructions, when executed by the one or more processors, further cause the one or more processors to:

determine at least one of a recommended amount of insulin or a recommended amount of carbohydrates for the patient; and present the at least one of a recommended amount of insulin or a recommended amount of carbohydrates for the patient on a display of the device.

* * * * *